United States Patent
Yang et al.

(10) Patent No.: US 7,616,303 B2
(45) Date of Patent: Nov. 10, 2009

(54) SYSTEMS AND METHODS FOR CORRECTING OPTICAL REFLECTANCE MEASUREMENTS

(75) Inventors: Ye Yang, Worcester, MA (US); Babs R. Soller, Northboro, MA (US); Olusola O. Soyemi, Shrewsbury, MA (US); Michael A. Shear, Northbridge, MA (US)

(73) Assignee: University of Massachusetts, Boston, MA (US)

( * ) Notice: Subject to any disclaimer, the term of this patent is extended or adjusted under 35 U.S.C. 154(b) by 275 days.

(21) Appl. No.: 11/411,538

(22) Filed: Apr. 25, 2006

(65) Prior Publication Data

US 2007/0038041 A1 Feb. 15, 2007

Related U.S. Application Data

(60) Provisional application No. 60/674,379, filed on Apr. 25, 2005.

(51) Int. Cl.
*G01J 3/00* (2006.01)
(52) U.S. Cl. .................. 356/300; 356/326; 600/310
(58) Field of Classification Search .......... 356/326; 600/310, 300, 336, 322, 323, 473, 476, 306, 600/360; 606/9, 10, 11, 12
See application file for complete search history.

(56) References Cited

U.S. PATENT DOCUMENTS

| | | | |
|---|---|---|---|
| 5,770,454 A | 6/1998 | Essenpreis et al. | |
| 7,130,672 B2* | 10/2006 | Pewzner et al. | 600/324 |
| 7,217,266 B2* | 5/2007 | Anderson et al. | 606/12 |
| 2005/0002031 A1* | 1/2005 | Kraemer et al. | 356/337 |
| 2007/0135844 A1* | 6/2007 | Balzano | 607/1 |

\* cited by examiner

*Primary Examiner*—Gregory J Toatley, Jr.
*Assistant Examiner*—Abdullahi Nur
(74) *Attorney, Agent, or Firm*—Fish & Richardson, P.C.

(57) ABSTRACT

We disclose measurement systems and methods for measuring analytes in target regions of samples that also include features overlying the target regions. The systems include: (a) a light source; (b) a detection system; (c) a set of at least first, second, and third light ports which transmit light from the light source to a sample and receive and direct light reflected from the sample to the detection system, generating a first set of data including information corresponding to both an internal target within the sample and features overlying the internal target, and a second set of data including information corresponding to features overlying the internal target; and (d) a processor configured to remove information characteristic of the overlying features from the first set of data using the first and second sets of data to produce corrected information representing the internal target.

37 Claims, 18 Drawing Sheets

SYSTEMS AND METHODS FOR CORRECTING OPTICAL REFLECTANCE MEASUREMENTS

CROSS-REFERENCE TO RELATED APPLICATIONS

This application claims priority to U.S. Provisional Application No. 60/674,379 entitled "SYSTEMS AND METHODS FOR CORRECTING OPTICAL REFLECTANCE MEASUREMENTS", filed on Apr. 25, 2005, the entire contents of which are incorporated herein by reference.

STATEMENT AS TO FEDERALLY SPONSORED RESEARCH

Funding for the work described herein was provided by the National Space Biomedical Research Institute, Grant Number SMS00403, funded under NASA Cooperative Agreement NCC 9-58 and the U.S. Army Congressionally Directed Medical Research Program, Grant Number DAMD17-03-1-0005. The Federal Government may have certain rights in the invention.

TECHNICAL FIELD

This invention relates to spectrometer systems and methods, and more particularly to spectrometer systems for reflectance measurements.

BACKGROUND

Optical spectroscopy can be used to determine the concentration of chemical species in gaseous, liquid, and solid samples. The amount of light absorbed by a particular chemical species is often linearly related to its concentration through Beer's Law, $A=\epsilon lc$, where A is the absorbance of the chemical species, $\epsilon$ is a constant specific to the chemical, l is the path length of light, and c is the concentration of the chemical. When incident light with an intensity, $I_0$, is incident on the sample, and I is the intensity of light after it has passed through a solution containing the chemical to be measured, the absorbance is given by $A=\log(I_0/I)$.

For nontransparent materials, including complex materials such as powders, tablets, natural materials (e.g., soil, agricultural products), blood, skin, and muscle, optical information can be collected via diffuse reflectance spectroscopy. In this setting, $A=(I_{100}/I_R)$, where $I_{100}$ is the light reflected from a 100% diffuse reflectance standard, the equivalent of the incident light, and $I_R$ is the light reflected from the sample under study. The concentration of a chemical component in one of these complex materials is related to A, though often not linearly. More sophisticated mathematical techniques, such as, for example, partial least squares regression and other multivariate calibration methods are used to determine a relationship between concentration and absorbance. Once these calibration models are derived, they can be used to determine chemical composition by measuring absorbance in transmittance or reflectance mode.

Diffuse reflectance spectroscopy techniques with near infrared spectroscopy ("NIRS") have been used for the noninvasive measurement of blood and tissue chemistry in human and animal subjects. NIRS (e.g., using a wavelength range of about 650-1000 nm) can be used to measure a number of important medical parameters such as tissue oxygenation, tissue pH, blood hematocrit ("Hct"), and glucose, but its widespread application in medicine has been hindered by both the inter- and intra-subject analyte-irrelevant variation in tissue overlying as well as inside the structures to be measured. For example, when diffuse reflectance NIRS is used to measure blood hematocrit in muscle or organs, the accuracy of the measurements can be affected by absorbance variations in layers overlying the muscle or organs (e.g., due to variations in the thickness of fat and skin layers between different patients in a patient population or between different locations on an individual patient) and/or spectral interference from structural variations in muscle and/or organs that are irrelevant to the measurements.

Near infrared light can penetrate through a subject's skin and bone to provide information on chemical species present in blood and underlying tissue. For example, pulse oximetry, a ubiquitous hospital monitoring system that measures arterial hemoglobin oxygen saturation, is based on two-wavelength NIRS. Multi-wavelength NIRS, in combination with chemometrics (i.e., statistics-based methods of analyzing complex spectra), can provide a platform technology for the noninvasive measurement of several additional analytes present in the blood and tissue. NIRS can provide accurate and continuous measurement of medical analytes without the need to remove a blood or tissue sample from the patient. The application of this technique involves shining near infrared light onto the skin directly or through a fiber optic bundle and measuring the spectrum of the light that is reflected back from the blood containing muscle. While near-infrared absorption by hemoglobin and deoxyhemoglobin has been used to measure oxygen saturation levels in various tissue beds, multi-wavelength spectroscopy in combination with additional mathematical techniques often is required to measure additional important blood and tissue analytes. Chemometrics is a branch of chemistry that provides statistics-based techniques to process multi-wavelength spectra such that analyte concentration can be calculated from the reflectance spectra recorded from complex media such as biological tissue.

Chemometrics is used to derive a mathematical relationship between relevant portions of the spectra collected from a sample and the concentration or amount of the analyte of interest in the sample. The relationship between the spectra and the chemical concentration can be expressed as a "calibration equation" that can be programmed into a patient monitor and used to determine analyte concentrations based on the measured reflectance spectra. Spectra collected from patients can be processed through calibration equation(s) stored in the patient monitor, and the analyte concentration in those patients can be reported based on the collected spectra and the calibration equations. Because the optical reflectance technique is noninvasive, the medical measurement can be updated as often as spectra are collected, usually on the order of a few seconds. The feasibility of using this method has been demonstrated on the bench, in animals, and in human subjects for the assessment of blood hematocrit, glucose, cholesterol, electrolytes, lactate, myoglobin saturation, muscle pH, and oxygen tension ("$PO_2$").

When calibration equations are developed using chemometrics, at least two sets of data are collected. A set of NIRS spectra is recorded approximately simultaneously with an independent, reliable measurement of the analyte over the entire physiologic and pathophysiologic range. For example, if one wanted to develop a calibration equation to determine blood hematocrit from measured reflectance spectra, several spectra from subjects would be compared with blood samples taken from those subjects and analyzed for hematocrit in a clinical laboratory. A chemometric technique, such as, for example, partial least squares ("PLS") regression can be used to identify and correlate portions of the spectrum to the measured hematocrit. The regression coefficients are used to generate the calibration equation.

Then, when subsequent reflectance spectra are collected from other patients, the regression coefficients can be combined with the spectra of the other patients to produce the NIRS-determined hematocrit value for the other patients. An advantage of using a chemometric technique such as PLS to derive a calibration equation, rather than simple linear regression, is that PLS is adept at establishing correlation between spectra and analytes when the analyte spectra are complicated by other absorbing species and scattering elements (like cells and muscle fibers).

For the calibration equation to perform accurately on patients over a wide range of instrumental and environmental conditions and different patient characteristics, the data in the calibration data set should cover as wide a range of values as possible and should encompass the entire clinically significant range. It is also important that the data be collected under the type of variable patient conditions that might affect the NIRS spectra. Conditions that affect spectra include variation in temperature, water content, and the presence of interfering chemical agents used to treat the patient. This helps ensure that the calibration equations are accurate when used on future subjects, because the effect of the interfering agents is modeled as part of the calibration equation.

Widespread application of NIRS for medical measurement has been hampered by both inter- and intra-subject variation in tissue overlying the target tissue, such as muscle, or the target organ. Additionally, NIRS measurement techniques have been limited by their inaccurate performance due to short-term changes in skin blood flow or due to long-term variation in skin surface and texture during wound healing.

SUMMARY

The invention is based, at least in part, on the discovery that when a spectrometer is used to record reflectance spectra from a sample, a short distance between the light source used to illuminate the sample and the detector used to measure reflected light results in recording of spectra that are sensitive to features that are relatively close to the surface of the sample, while a longer source-detector distance results in spectra that are sensitive to both surface features and deeper lying (e.g., internal) features of the sample. Correcting spectra recorded with a long source-detector spacing against spectra recorded with a short source-detector spacing can remove the spectral features of the overlying features from the spectra of the internal, deeper lying features. The spectra can be further corrected to remove features that arise from variations in optical scattering properties of the internal features that are not related to measurements of an analyte of interest in the underlying layers.

Spectra can be recorded using light of different wavelengths. For example, the light source can provide light in one or more of the near-infrared, infrared, visible, ultraviolet, and other regions of the electromagnetic spectrum.

In a first aspect, the invention features measurement systems that include: (a) a light source; (b) a detection system; (c) a set of at least first, second, and third light ports which transmits light from the light source to a sample and receives and directs light reflected from the sample to the detection system, where a distance between the first port and the third port corresponds to a first detection distance, a distance between the second port and the third port corresponds to a second detection distance, and the first detection distance is larger than the second detection distance; and (d) a processor. Either (i) the first and second ports are transmitting ports and the third port is a receiving port, or (ii) the first and second ports are receiving ports and the third port is a transmitting port. The detection systems generate a first set of data corresponding to the first detection distance and including information corresponding to both an internal target within the sample and features overlying the internal target, and a second set of data corresponding to the second detection distance and including information corresponding to features overlying the internal target. The processor is configured to remove information characteristic of the overlying features from the first set of data using the first and second sets of data to produce corrected information representing the internal target.

Embodiments can include any of the following features.

The set of at least first, second, and third ports can be situated on a single probe. The second detection distance can be between about 1 mm and about 5 mm, for example, such as between about 1.5 mm and about 3.5 mm. The first detection distance can be greater than about 10 mm (e.g., greater than about 15 mm, greater than about 20 mm, greater than about 30 mm, greater than about 50 mm). The system can include a shutter system for controlling whether light from the first or second transmitting port illuminates the sample.

The probe head can include a thermally conductive material to dissipate heat from the sample. The system can further include a thermally-conductive bridge between light transmitting ports and light receiving ports.

The light source can provide light in the near-infrared region of the electromagnetic spectrum. The light source can include at least one of an incandescent light source element, a light emitting diode, a laser diode, and a laser. For example, the light source can include an array of light emitting diodes.

The detection system can be a spectral detection system, the first and second sets of data can include first and second sets of spectra, and the processor can remove spectral information characteristic of the overlying features from the first set of spectra using the first and second sets of spectra to produce corrected spectral information representing the internal target. The spectral detection system can include a spectrometer configured to receive light and to generate sets of spectra from the received light. Alternatively, the spectral detection system can include a first spectrometer configured to receive light from the first receiving port and to generate the first set of spectra, and a second spectrometer configured to receive light from the second receiving port and to generate the second set of spectra.

The processor can be configured to remove spectral information from the first set of spectra that is characteristic of variations in optical scattering properties of the internal target that are unrelated to an analyte of interest therein. The processor can be configured to remove spectral information from the corrected spectral information representing the internal target that is characteristic of variations in optical scattering properties of the internal target that are unrelated to an analyte of interest therein. The processor can be configured to remove spectral information characteristic of the overlying features from the first set of spectra using the first and second sets of spectra according to the equation $$\hat{R}_{ort} = R_{sfm} - \tilde{R}_{sf} w^T$$

where $R_{sfm}$ is a spectrum from the first set of spectra, $\tilde{R}_{sf}$ is a spectrum from the second set of spectra, w is a weight, "T" denotes a matrix transpose operation, and $\hat{R}_{ort}$ comprises corrected spectral information representing the internal target. The processor can be further configured to normalize the first and second sets of spectra with respect to one another prior to producing the corrected spectral information.

The processor can be configured to remove spectral information that is characteristic of variations in optical scattering properties of the internal target from the first set of spectra by orthogonalizing the first set of spectra with respect to a set of loading vectors of principal components determined from a set of spectra from a plurality of samples. The plurality of samples can have a property of the internal target within a selected range. For example, the property of the internal target can be a value of an analyte such as pH, hematocrit, tissue oxygenation, or another property. The range can be selected to facilitate correction and/or analysis of the spectra. For example, a selected range for pH can be 7.37±0.001 pH units The processor can be configured to orthogonalize the first set of spectra by performing a set of steps that include: (a) performing a principal component analysis on a set of calibration spectra to determine a set of loading vectors corresponding to principal components of the calibration spectra; (b) determining one or more orthogonalization factors from the principal component analysis; (c) forming a loadings matrix having at least one dimension equal to the number of orthogonalization factors; and (d) orthogonalizing the first set of spectra with respect to the loadings matrix.

In another aspect, the invention features methods for correcting information corresponding to an internal target within a sample measured by a system having a light source, a detection system, and a set of at least first, second, and third light ports which transmits light from the light source to the sample and receives and directs light reflected from the sample to the detection system, where a distance between the first port and the third port corresponds to a first detection distance and a distance between the second port and the third port corresponds to a second detection distance, where the first detection distance is larger than the second detection distance, and where either (i) the first and second ports are transmitting ports and the third port is a receiving port, or (ii) the first and second ports are receiving ports and the third port is a transmitting port. The methods include: (a) illuminating the sample with one or more light ports of the set; (b) detecting the reflected light with the detection system; (c) generating a first set of data corresponding to the first detection distance and including information corresponding to both an internal target within the sample and features overlying the internal target, and a second set of data corresponding to the second detection distance and including information corresponding to features overlying the internal target; and (d) removing information characteristic of the overlying features from the first set of data using the first and second sets of data to produce corrected information representing the internal target.

Embodiments of the methods can include any of the following features.

The detection system can be a spectral detection system, the first and second sets of data can include first and second sets of spectra, and removing information characteristic of the overlying features from the first set of data can include removing spectral information characteristic of the overlying features from the first set of spectra using the first and second sets of spectra to produce corrected spectral information representing the internal target. Removing spectral information characteristic of overlying features of the sample from the first set of spectra can include combining the first and second sets of spectra according to the equation $$\hat{R}_{ort} = R_{sfm} - \tilde{R}_{sf} w^T$$

where $R_{sfm}$ is a spectrum from the first set of spectra, $\tilde{R}_{sf}$ is a spectrum from the second set of spectra, w is a weight, "T" denotes a matrix transpose operation, and $\hat{R}_{ort}$ includes corrected spectral information representing the internal target.

The methods can further include normalizing the first and second sets of spectra relative to one another prior to producing the corrected spectral information. Normalizing the sets of spectra can include applying a polynomial fit between the first and second sets of spectra. Coefficients used in the polynomial fit can be derived from first and second sets of spectra recorded from one or more reflectance standards.

The methods can include processing the first set of spectra to remove spectral information characteristic of variations in optical properties of the internal target that are unrelated to an analyte of interest therein. The methods can include processing the corrected spectral information representing the internal target to remove spectral information that is characteristic of variations in optical scattering properties of the internal target that are unrelated to an analyte of interest therein. Removing spectral information characteristic of variations in optical properties of the internal target that are unrelated to an analyte of interest therein can include orthogonalizing the first set of spectra with respect to a set of loading vectors of principal components determined from a set of calibration spectra.

Orthogonalizing the first set of spectra with respect to a set of loading vectors can include: (a) performing a principal component analysis on a set of calibration spectra to determine a set of loading vectors corresponding to principal components of the set of calibration spectra; (b) determining one or more orthogonalization factors from the principal component analysis; (c) forming a loadings matrix having at least one dimension equal to the number of orthogonalization factors; and (d) orthogonalizing the first set of spectra with respect to the loadings matrix.

In another aspect, the invention features methods of measuring an analyte in a subject by: (a) generating a set of corrected spectra based on reflectance measurements from an animal according to the methods disclosed herein; (b) developing one or more calibration equations based on a relationship between a measurement of the analyte in the animal and the set of corrected spectra from the animal; (c) generating a set of corrected spectra based on reflectance measurements from the subject according to the methods disclosed herein; and (d) determining a value of the analyte in the subject based on the one or more calibration equations and the set of corrected spectra from the subject. The subject can be a human, for example. The sets of corrected spectra can be generated based on reflectance measurements from the animal and the subject are further processed to remove spectral information characteristic of variations in optical properties of internal targets comprising the analyte.

The invention also features methods of measuring an analyte in a subject by: (a) generating a set of corrected spectra based on reflectance measurements from a first body site of the subject according to the methods disclosed herein; (b) developing one or more calibration equations based on a relationship between a measurement of the analyte at the first body site and the set of corrected spectra from the first body site; (c) generating a set of corrected spectra based on reflectance measurements from a second body site of the subject according to the methods disclosed herein; and (d) determining a value of the analyte at the second body site based on the one or more calibration equations and the set of corrected spectra from the second body site. The subject can be a human, the first body site can be an arm, and the second body site can be a leg. The sets of corrected spectra generated based on reflectance measurements from the first and second body sites can be further processed to remove spectral information characteristic of variations in optical properties of internal targets comprising the analyte.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

Like reference symbols in the various drawings indicate like elements.

DETAILED DESCRIPTION

General Methodology

Figure 1:
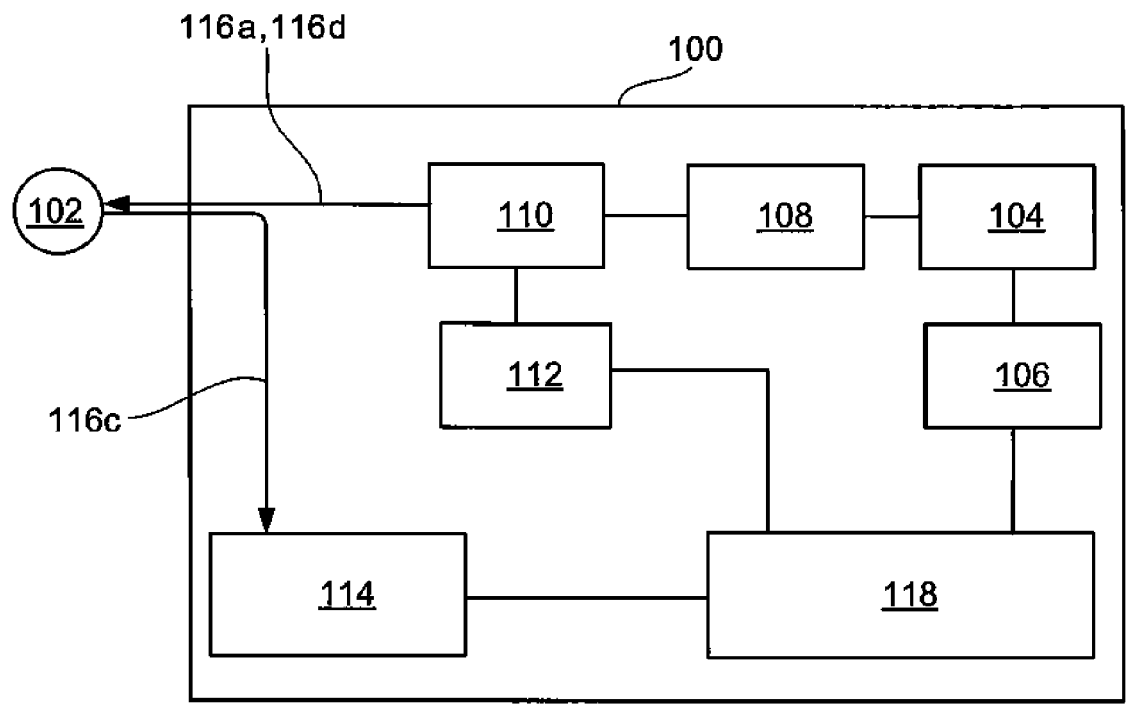
FIG. 1 is a schematic diagram of a spectrometer system described herein.

As described herein, a new fiber optic sensor and associated processor programmed and configured to perform certain mathematical algorithms are used to extend the applicability of NIRS for the noninvasive measurement of blood and tissue chemistry. The sensor is designed and used to remove the interfering spectral influence of one or more tissues that are not of interest, such as skin and fat, that overlay tissues of interest and complicate measured signals from those tissues, such as scattering from muscle tissue and/or from tissue of an organ in a patient, thus permitting greater generalization of chemometrics-based calibration equations. In particular, the sensor has a detection port for detecting light scattered and reflected from a patient and at least two illumination ports that are located at different distances from the detection port. Light from an illumination port that is close to the detection port causes a reflectance spectrum that is due mainly to the overlying fat and skin layers, while light from an illumination port that is more distant from the detection port causes a reflectance spectrum that is due to the combination of reflections from the overlying skin and fat layers as well as deeper muscle and/or organ layers. Information in the two spectra and generalized chemometrics-based calibration equations can be used to extract chemical information about just the tissue of interest, e.g., the underlying muscle and/or organ layer.

The sensor can also be used to reduce and/or remove interfering spectral influences that arises due to sample-to-sample structural variations in tissues of interest. For example, the sensor can be used to measure a particular analyte in one or more muscle tissue layers that underlie skin and fat layers. After removing the spectral influence of the skin and fat layers from measured reflectance spectra, additional steps can be performed by the sensor to remove spectral influences that arise from variations in optical properties of the muscle tissue. For example, optical properties of the muscle tissue can vary according to a surface texture, and/or a capillary density, and/or a fiber structure, and/or other structural properties of the muscle tissue. Variations in optical properties of the tissues of interest typically affect an optical scattering coefficient of the tissue.

By generalizing the calibration equations based on corrected reflectance spectra, the sensor can be used to perform accurate measurements when placed on muscle or other tissue sites different from those used for calibration development, and calibration equations developed from animal models of pathophysiology can be applied to human subjects with clinically acceptable results. The methods can also be applied during clinical measurement to continually correct for varying patient conditions that will alter spectra, such as skin blood flow and surface changes which occur during wound healing.

The new devices and techniques described herein are aimed at reducing spectral interference from overlying tissue such as skin and fat on the spectra measured from underlying muscle and/or organs. When successfully implemented, calibration equations developed using these devices and techniques can be applied to spectra acquired from almost any anatomical site, irrespective of the optical properties of the overlying layer(s). Further, the new devices and techniques are aimed at reducing spectral interference from structural variations in tissues of interest that are not correlated to measurements of a specific analyte within the tissues of interest. Calibration equations developed based on spectra that are corrected for structural variations in tissues of interest, e.g., variations that affect the optical properties of tissues of interest, can be applied to different measurement regions on a single measurement subject, and/or to different measurement subjects. For example, calibration equations developed based on measurements performed on a patient's arm, which has a thin fat and skin layer, can be applied to spectra collected from the patient's leg, which has a thicker fat and skin layer.

With a powerful light source and a sensitive detector, the devices and techniques described herein allow accurate spectra to be collected from internal organs by reducing spectral interference from overlying skin, fat, and muscle layers, and from structural variations in the internal organ tissues. Another advantage of the new approaches is the ability to continually compensate for changing patient conditions such as variation in skin blood flow and surface texture. By removing spectral interference from the overlying layers from the spectra of the underlying layers, variations in the overlying layer spectra will cause little variation in the measured information of the underlying layers obtained from the reflectance spectra. By removing spectral interference from structural variations in tissues of interest (e.g., the underlying layers), variations in the structure of the tissues of interest will contribute only relatively small variations to measured information for selected analytes in the tissues of interest. These spectral interference corrections permit a more accurate determination of important blood and tissue chemistry parameters from patients.

In-vivo calibration requires access to patients who have variation in the analyte to be measured and offer the same or similar pathophysiology as expected in future application of the devices and techniques. Often, it is difficult to obtain access to a sufficient number of subjects and even when they are available, the variation may not be large enough to encompass the entire pathophysiological range for the parameter that is sought to be modeled and measured. Another issue is how to incorporate the potential spectral interference from new treatment methods. For instance, when developing methods of measuring muscle pH to help guide resuscitation of a patient from shock, it may be necessary to update the calibration equation used for determining muscle pH to account for new therapeutic agents used when the patient is in shock. However, deliberately placing human test subjects in shock to develop updated calibration equations is not possible. A superior method for developing robust calibration equations that span large ranges of medical parameters and that can be altered for new conditions and drugs would be to develop calibration equations on animals and transfer them directly to humans. By using animals it is possible, for instance, to observe variations in analyte values caused by serious shock. This can be done on multiple animals to validate the sensor for this application before it is used on critically ill humans. Also some analytes are difficult to vary reliably in a clinical setting. However, the methods described herein will allow calibration equations developed on animals to be transferred successfully for use on human subjects. Once the spectral influence of the overlying tissue layers are removed, the muscle spectra of animals, such as swine, may be similar to those of human subjects. Spectral differences in human and animal muscle structure can be corrected using methods that remove these variations. Calibration equations derived from swine muscle can then be used for human subjects.

Overall System

As shown in FIG. 1, a portable, fiber-optic-based spectroscopic system 100 for measurement of reflectance spectra from a sample 102 located remotely from the system includes a lamp 104, a power supply for the lamp 106, an optical bench 108, a shutter system 110, a driver for the shutter system 112, a spectrograph 114, a fiber optic cable 116, and a computer 118. Light from the lamp is manipulated by optics within the optical bench 106 and can be controlled by a shutter system 110 that is driven by a shutter driver 112. Light can be passed selectively by the shutter system 110 into a first fiber optic cable 116a or a second fiber optic cable 116d that guide the light to the sample 102 to illuminate the sample.

When light is guided to the sample in the fiber optic cable 116a or 116d, light is reflected from the sample 102 and collected by a third portion of the fiber optic cable 116c that guides the reflected light from the sample 102 to the spectrograph 114. The reflected light is analyzed by the spectrograph 114 to gather information about the sample 102.

The spectrograph 114 can be a commercial portable spectrograph that can be operated by computer control. For example, an Ocean Optics USB2000 spectrograph with a grating optimized for performance in the wavelength range of 500-1000 nm can be used. The spectrograph detector can be a 2048 element shallow-well linear CCD-array. The spectrograph can be equipped with a 200 micron wide slit to increase resolution, a collection lens to increase light collection efficiency at the detector, and a long pass filter to block light with a wavelength less than 475 nm from reaching the detector. The USB2000 spectrograph interfaces with the computer 118, e.g., through either a USB or RS232 port.

The system 100 further includes an on-board computer 118 for controlling the shutter driver 112, the spectrograph 114, and for processing, storing, and displaying data from the spectrograph.

Figure 2:
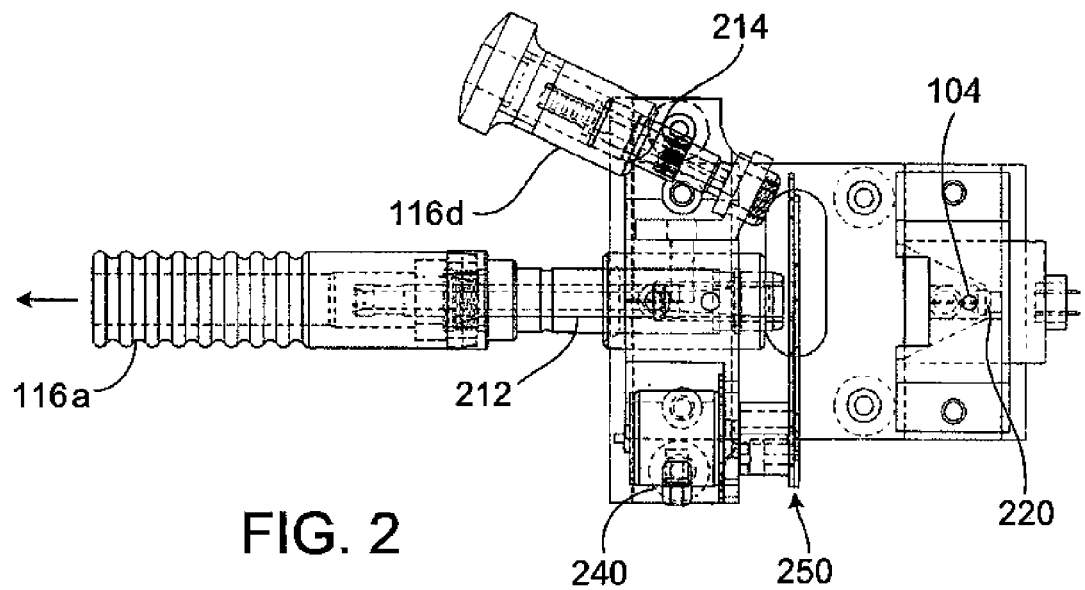
FIG. 2 is a top schematic view of an optical bench and selected components of the spectrometer system of FIG. 1.

As shown in FIG. 2, optical bench 108 includes several primary optical components of the system. An illumination lamp 104 provides light to illuminate the sample. A first optical connector 212 couples the light to a first fiber-optic cable 116a for carrying light to illuminate the sample 102. A second optical connector 214 couples light to a second fiber-optic cable 116d that carries light to illuminate the sample 102. A shutter 250 can select whether of the first fiber-optic cable 116a or the second fiber optic cable 116d is illuminated by the lamp light. Optical bench 108 is used to set up and maintain proper alignment of the above-mentioned optical components to enhance the accuracy and reproducibility of the system 100 as a reflectance spectroscopy measurement system. Optical bench 108 can be fabricated from aluminum because aluminum can be easily machined to close tolerances and has high thermal conductivity to promote heat dissipation and minimize thermal stress and distortion on the components of the system 100.

Lamp 104 can be a white light source (e.g., a tungsten-halogen 9 W bulb such as a Welch-Allyn 8106-001 bulb) that is driven by a specially designed power supply 106 to allow for fast ramp-up and stable operation of the lamp. The lamp 104 can be a continuous wave ("cw") light source or a pulsed light source. The lamp 104 is housed within its own machined reflector, so that it is relatively easy to replace when necessary, and its optical alignment is assured through the design of the optical bench. The lamp rests against mechanical stops that ensure that it is accurately located with respect to the fiber optic cables 116a and 116d. Light from the lamp 104 can be focused down a center axis of the optical bench 108 by a rear reflector 220 (e.g., an ellipsoidal reflector).

Figure 3:
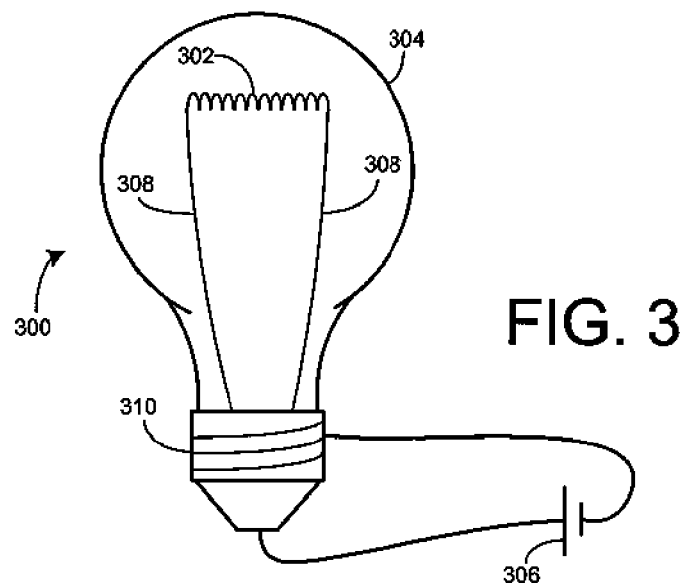
FIG. 3 is a schematic diagram of an incandescent lamp.

The general lamp configuration is illustrated in FIG. 3, which shows an incandescent light source 300 that includes an electrically resistive filament 302 within a transparent bulb 304. Filament 302 is generally made of tungsten. Bulb 304 can be made of glass, quartz, or other materials and can be evacuated or can be filled with a halogen gas, an inert gas, or a mixture of gases. Electrical current is supplied from a power supply 306 to the filament 302 through electrically conductive lead wires 308 that are electrically connected to a base 310 of the light source. The electrical current causes the filament to radiate as a black body. The power supply 306 can supply direct current (DC) or alternating current (AC). To ensure stable operation of the lamp 104 and a constant spectrum emitted from the bulb, the filament is driven by an electrical circuit that supplies current to the filament such that the temperature of the filament remains substantially constant, such that a stable blackbody radiation spectrum is emitted from the bulb.

Fiber Optic Cable System

Referring again to FIG. 1, light from the light source 104 can be used to excite an electromagnetic reflectance spectrum of the sample 102. Light can be ported from light source 104 to the sample 102 in fiber optic cables 116a and/or 116d to illuminate the sample and to excite the sample optically. Light reflected from the sample 102 can be collected and delivered from the sample in a fiber optic cable 116c to a spectrograph 114 that measures the reflectance spectrum of the sample 102. Illumination light in cable 116a exits the cable and is incident on sample 102 at a first distance (e.g., about 32 mm) from the entrance to the cable 116c that collects reflected light from the sample and guides the reflected light to the spectrograph 114 for analysis. Illumination light in cable 116d exits the cable and is incident on sample 102 at a second distance (e.g., about 2.5 mm) from the entrance to the cable 116c that is less than the first distance. Spectra from the sample that are collected when the sample is illuminated by light from cable 116a and from cable 116d can be used to extract detailed information about the sample, as explained below.

Referring to FIG. 2, the fiber-optic illumination cable 116a for illuminating the sample 102 can be positioned directly in front of the lamp 104 with the end of the fiber-optic cable 116a being at the focal point of the light emitted from the lamp 104. The cable 116a is inserted into position before system use, and a mechanical click stop ensures that the cable 116a is properly positioned and secured in relation to the lamp 104 and the reflector 220.

A second fiber optic cable 116d that also is used for illuminating the sample 102 is threaded into port 214 in the optical bench, e.g., at an angle to an optical axis of reflector 220 of between about 5 degrees and about 90 degrees (e.g., between about 10 degrees and about 60 degrees, between about 15 degrees and about 35 degrees) with respect to the focused beam axis. Placing the cable 116d into port 214 at an angle to the focused beam axis results in a reduced intensity of light entering the cable 116d, compared to an on-axis position of cable 116d. However, because cable 116d delivers light to the sample at a closer distance to detection cable 116c than cable 116a does, the amount of light reflected by the sample and collected in detection cable 116c can be similar whether the sample is illuminated with the higher intensity light from cable 116a or the lower intensity light in cable 116d.

Figure 4A:
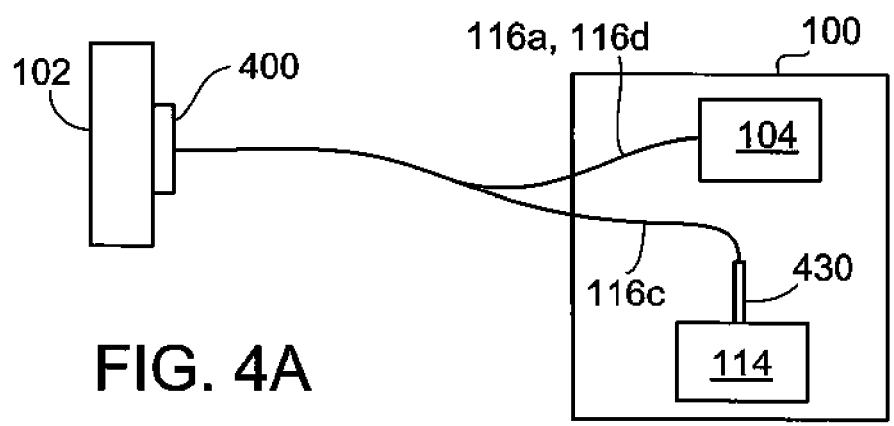
FIG. 4A is schematic diagram of an arrangement of two fiber optic cables for delivering light to a sample and a fiber optic cable for delivering reflected light from the sample to a spectrograph.

As shown in FIG. 4A, the fiber optic cable can include different fiber bundles 116a, 116c, and 116d. The cable holding the sample bundles 116a or 116d can be contained in a common protective sheath with the cable holding the return bundle 116c outside the unit 100 housing the spectrograph 114 and the light source 104. The sample bundles 116a, 116c, and 116d can be gathered together outside the housing of the system 100, which contains spectrograph 114 and the lamp 104, about 8-12 inches downstream from the housing. The cable containing the bundles 116a, 116c, and 116d connects spectrograph 114 and the lamp 104 to a probe head 400 that can be located at sample 102 to perform reflectance measurements on sample 102.

Figure 4B:
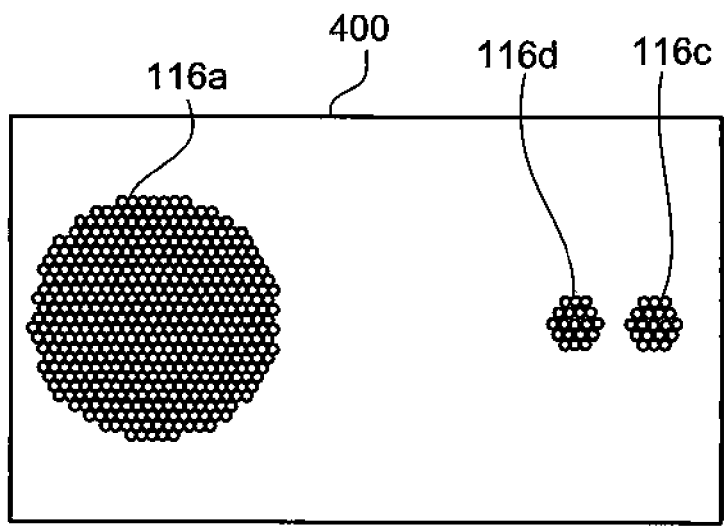
FIG. 4B is a schematic end view of an arrangement of fibers in the fiber optic cable for delivering light to the sample and fibers in the fiber optic cable for delivering reflected light from the sample to a spectrograph.

As shown in FIG. 4B, at the sample end of the cable system, a probe head 400 includes illumination bundles 116a and 116d, which are oriented perpendicular to a face of the housing 400 and perpendicular to a surface of sample 102. Housing 400 can hold the ends of illumination fiber bundle 116a, illumination fiber bundle 116d, and detection fiber bundle 116c. Fiber bundle 116a can contain approximately 2666, 50 µm glass fibers with a numerical aperture (NA) of about 0.66. The detection bundle of fibers in return cable 116c returns reflected light from the sample to the spectrograph 114, and in one embodiment can contain 109, 50 µm glass fibers with a NA of about 0.66. At the sample end of the fibers, the fibers are oriented perpendicularly to sample 102. Along the length of the fiber optic cable, between light source 104 and spectrograph 114 at one end and the sample 102 at the other end, the sample illumination bundle 116a that delivers light to the sample is optically shielded from the return bundle 116c with an opaque material, such as an opaque tape or plastic sheath or tube, so that any light that leaks out of illumination bundles 116a and/or 116d is not coupled into the return bundle 116c. To improve optical coupling between lamp 104 and sample fiber bundles 116a and 116d, a tapered NA converter can be placed at the end of sample cable bundles 116a and 116d to convert the 0.42 NA of the light source to the 0.66 NA of the fibers. This increases the collection efficiency into the fibers by about 15%.

To reduce the NA of the return fiber bundle to 0.22 as may be needed to ensure proper interfacing with spectrograph 114, a 600 µm diameter fused silica rod can be placed at the end of fiber bundle 116c. To prevent stray light from entering the spectrograph 114, a black, light-absorbing epoxy or other material can be used to surround the silica rod.

Figure 5A:
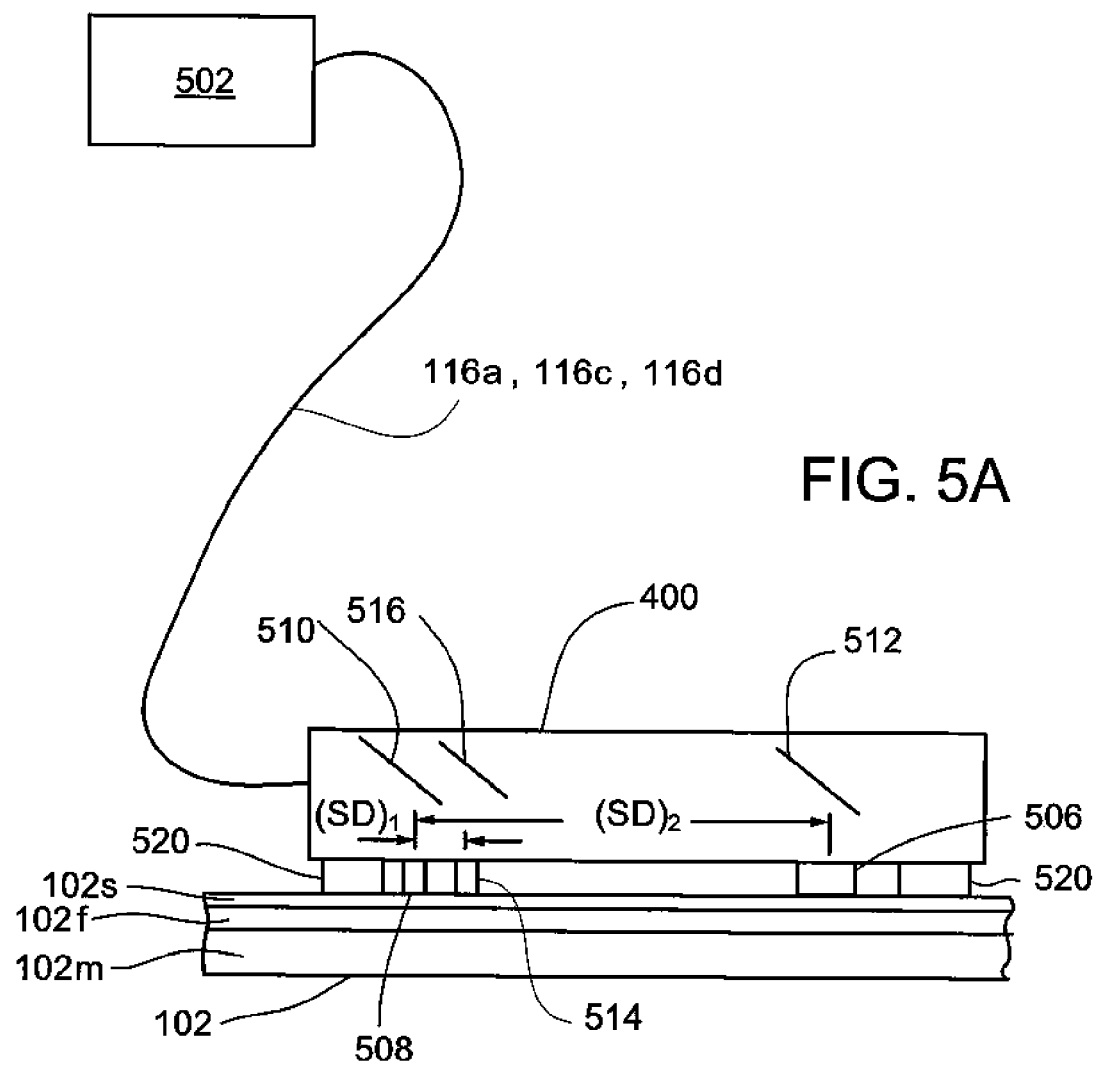
FIG. 5A is a schematic side view of an embodiment of a probe head for delivering light to a sample and for receiving reflected light from the sample.

As shown in FIG. 5, light can be delivered from the unit 502 housing the lamp 104 and the spectrograph 114 to the probe head 400 that delivers light to sample 102 in a fiber bundle 116a and/or 116d, and light scattered from the sample can be collected and routed back to spectrograph 114 in fiber bundle 116c. The bundles 116a, 116c, and 116d can be contained in a single cable that runs between housing unit 502 and probe head 400, and the cable can be several meters long to allow convenient access to and data collection from a sample or a patient. To minimize cross talk between light illumination bundles 116a and 116d and light detection bundle 116c, bundles 116a and 116d delivering illumination light from lamp 104 to sample 102 can be wrapped in black tape or other opaque material so that any leaked light does not couple into light return bundle 116c.

As shown in FIG. 5, probe head 400 can have an illumination light port 506 for delivering light to the sample that is spatially separated by a distance $(SD)_2$ from a detection light port 508 for receiving light from the sample. Fiber bundle 116a can be coupled horizontally into probe head 400, and light from bundle 116a can be reflected from a 45 degree mirror 510 within the probe head and directed vertically towards sample 102 from light port 506. Similarly, light scattered from sample 102 can be collected by light port 508 and reflected by a mirror 510 into detector fiber bundle 116c. Alternatively, fiber bundles 116a and 116c can enter probe head 400 horizontally and then bend 90 degrees in a vertical direction such that they are directly coupled to light ports 506 and 508, respectively.

Illumination light port 506 can contain a 3.5 mm bundle of 50 µm glass fibers having an overall NA of 0.66 for directing light from housing unit 502 to sample 102. Sample 102 can include a top layer (e.g., a skin layer) 102s, an overlying layer (e.g., a fat layer) 102f, and an underlying layer (e.g., a muscle layer) 102m, and light can be reflected from any or all of the layers to the detector fiber bundle 116c. Detection light port 508 that is coupled to bundle 116c is spaced a distance of between about 10 mm and about 100 mm (e.g., between about 20 mm and about 50 mm, between about 30 mm and about 40 mm, between about 30 mm and about 32 mm) from illumination light port 506, and directs diffusely reflected light from the sample to unit 502 housing spectrograph 114, where the reflected light can be analyzed. Light port 508 can have a 1 mm diameter detection bundle of 50 µm glass fibers with a collective NA of 0.66.

Probe head 400 can include an additional illumination light port 514 configured similarly to first illumination light port 506, but located closer to detection light port 508 than first illumination light port 506, at a distance $(SD)_1$. The distance $(SD)_1$ can be between about 1 mm and about 5 mm (e.g., about 1.5 mm, about 2.5 mm, about 3 mm, about 4 mm). For example, the center of the 1 mm fiber bundle of second illumination light port 514 can be located about 2.5 mm from the center of the 1 mm diameter fiber bundle of detection light port 508, while the 3.5 mm diameter fiber bundle of first illumination light port 506 can be located about 30 mm from the center of detection light port 508. A diameter of light port 514 can be smaller than a diameter of light port 506, so that, although more light is incident on sample 102 from the light port 506 than from light port 514, approximately the same reflected intensity is collected by detection light port 508 regardless of whether the sample is illuminated with light from illumination port 506 or 514. Having similar intensities in the reflected spectra whether the sample is illuminated with light from illumination port 506 or 514 permits a good signal-to-noise ratio to be obtained without having to integrate on the detector for a longer time when light from one of the two illumination ports is used.

The respective spacings between the two illumination light ports 506 and 514 and the detection light port 508 ($(SD)_1$ and $(SD)_2$) are chosen in conjunction with the intensity and spectrum of the light emitted from illumination light ports 506 and 514 and the reflectance spectrum of sample 102 to obtain particular information about sample 102. For example, spectroscopic system 100 can be used to direct near infrared radiation (e.g., radiation having a wavelength of 700-1000 nm) through a human patient's skin to permit direct, noninvasive measurement of blood chemistry or chemistry in tissue beneath the skin without removing a blood or tissue sample from the patient. In particular, system 100 can be used to measure muscle pH, muscle oxygen tension $(PO_2)$, and blood hematocrit from continuous wave near infrared spectra obtained with the system. Shorter distance $(SD)_1$ should be selected to properly induce reflection only from tissue that is not of interest, such as skin and fat overlying a tissue of interest, such as muscle or tissue of an organ. As indicated below, this distance has been calculated for overlying skin and fat, where muscle is the tissue of interest.

To record spectral information from a human patient, thermally conducting feet 520 of probe head 400 are placed in contact with a portion of the patient's body, light is directed from illumination ports 506 and/or 514 to the patient, and reflected light is collected in detection port 508. For example, feet 520 of probe head 400 can be placed in contact with the skin on the surface of a patient's forearm, so that light can be emitted from illumination light ports 506 and/or 514, reflected from tissue within a portion of the patient's body (e.g., the patient's hand, forearm, calf, thigh, stomach, or chest) and collected via detection light port 508. To record information from the patient's muscle, light from illumination light ports 506 and/or 514 penetrates through skin layer 102s and fat layer 102f, which is generally between about 3 mm and about 10 mm thick (e.g., between about 4 mm and about 5 mm thick), to reach muscle layer 102m, and then the light is scattered from the muscle layer and collected in detection light port 508. In some embodiments, second illumination light port 514 and detection light port 508 can be located together in one thermally conducting foot 520, e.g., in embodiments involving detection of analytes in human muscle.

Using lamp 104, e.g., an 8 Watt lamp, about 7 lumens of light can be emitted from a 3.5 mm diameter illumination light port 506 or 514, or about 25 lumens of light can be emitted from a 6 mm diameter illumination light port. It has been determined empirically that a spacing of about 30 mm between illumination light port 506 and detection light port 508 allows light collected in detection light port 508 to include a significant signal due to light scattered from muscle tissue 102m underlying skin and fat layers 102s and 102f. When light is emitted from second illumination light port 514 that is positioned closer to detection light port 508 than first illumination light port 506, the light collected in detection light port 508 includes a significant signal from light scattered from the overlying skin and fat layers 102s and 102f. This second signal can be used to remove signal components that arise due to scattering and/or absorption from the overlying skin/fat layers 102s and 102f in the overall signal recorded when the patient's arm is illuminated with light from first illumination light port 506. Light emitted from the two illumination light ports 506 and 514 can originate from the same lamp 104, and shutter 250 can be used to control emission of light from each of first illumination light port 506 and second illumination light port 514, as explained in more detail below.

Two signals corresponding to light scattering from shallow skin/fat layers 102s and 102f and from deeper muscle layer 102m can also be obtained by using a single illumination light port and two light detection ports, one of which is located closer to the illumination light port than the other.

Probe head 400 and its feet 520 can be made of a thermally-conductive material (e.g., aluminum or copper) to conduct heat away from a patient's skin. If the probe head is made of non-conductive material (e.g., plastic), heat delivered though illumination light ports 506 and/or 514 can be sufficient to dilate blood vessels in the skin and alter skin blood volume of the patient. This effect of heat on skin blood flow can change a reflectance spectrum recorded from the patient. A thermal conductor in probe head 400 provides a thermal bridge between feet 520 at opposite ends of probe head 400, so that the temperature of a patient's tissue is substantially the same in the vicinity of the two illumination ports 506 and 514 and detection port 508.

Figure 5B:
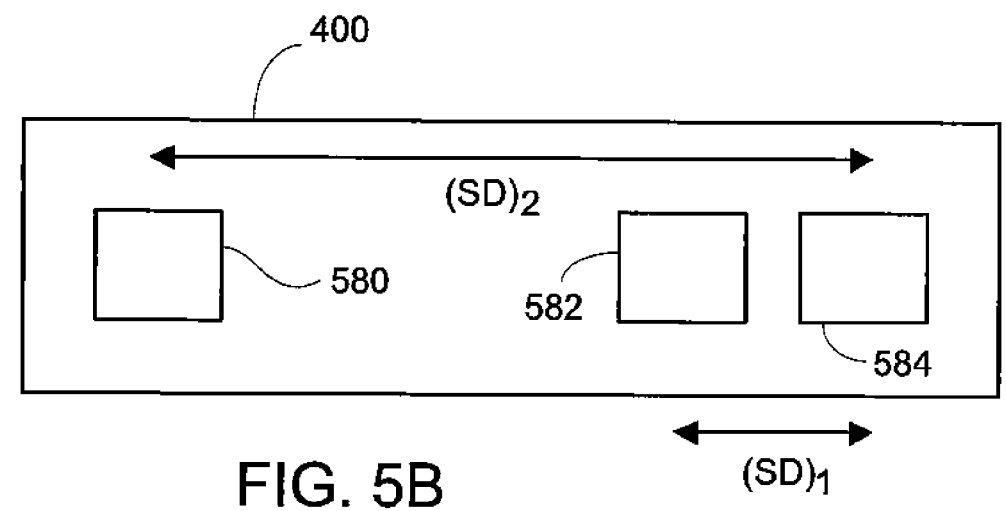
FIG. 5B is a schematic bottom view of an embodiment of a probe head with integrated light sources.

Referring to FIG. 5B, in some embodiments, the light source can include one or more light-emitting diodes. Probe head 400 includes a first light source 580 positioned within probe head 400 to form an illumination port at a distance $(SD)_2$ from detection port 584. Probe head 400 also includes a second light source 582 positioned within probe head 400 to form an illumination port at a distance $(SD)_1$ from detection port 584. Light sources 580 and 582 do not include fiber optic cables or other coupling elements, and are positioned such that light from each of the sources illuminates a sample directly. Light reflected by the sample is received by the system via detection port 584.

Light sources 580 and 582 can each include an array of light emitting diodes (LEDs). A number and spatial distribution of the LEDs can be selected to provide a particular reflected light intensity in detection port 584 from each source. For example, light source 580 can include a relatively densely packed array of LEDs, and light source 582 can include a less densely packed array of LEDs, so that the reflected light received in detection port 584 from each of the two sources is approximately equal in intensity.

LEDs used in light sources 580 and/or 582 can provide light in varying regions of the electromagnetic spectrum. For example, LEDs can provide light having wavelengths in the visible and/or ultraviolet and/or near-infrared and or infrared regions of the spectrum. LEDs can also provide light in other regions of the spectrum, and in multiple regions of the spectrum at the same time. In some embodiments, multiple different types of LEDs having different light emission properties (e.g., wavelength, intensity, and other properties) can be provided in a single light source, such as light source 580 and/or light source 582.

In certain embodiments, light sources 580 and/or 582 can include other types of sources (e.g., incandescent sources, laser-based sources) integrated in probe head 400 or coupled to probe head 400. Detectors such as spectrometers can be incorporated into probe head 400, or can be optically coupled to probe head 400, e.g., using a fiber optic cable.

Figure 6A:
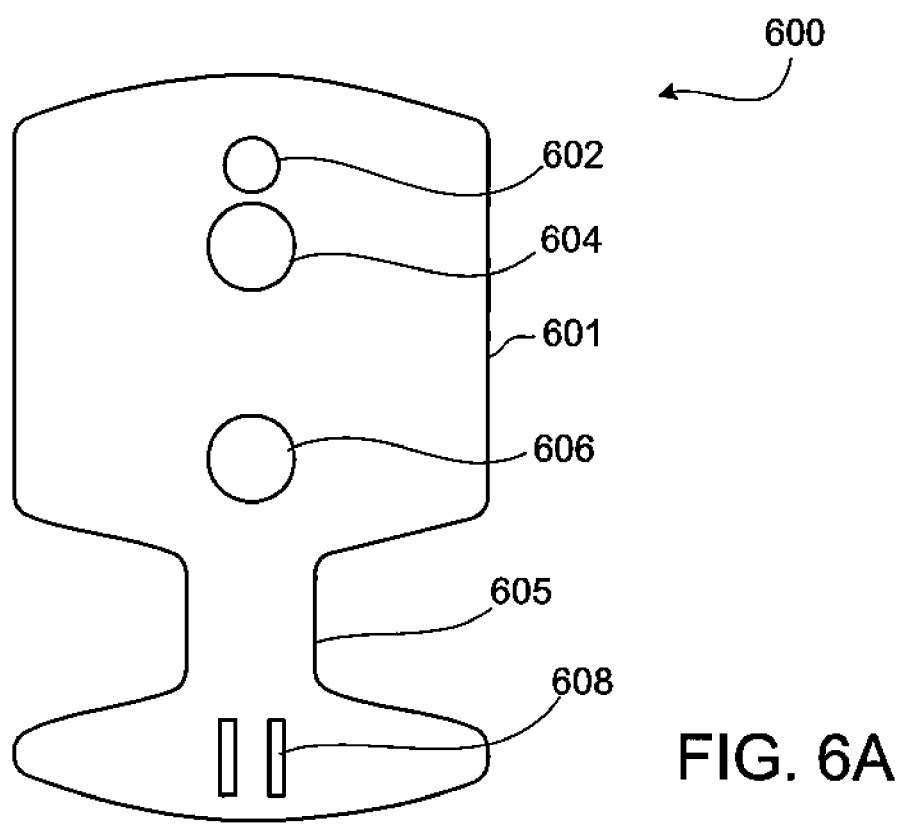
FIG. 6A is a schematic top view of a light shield for holding and shielding the probe head shown in FIG. 5.
Figure 6B:
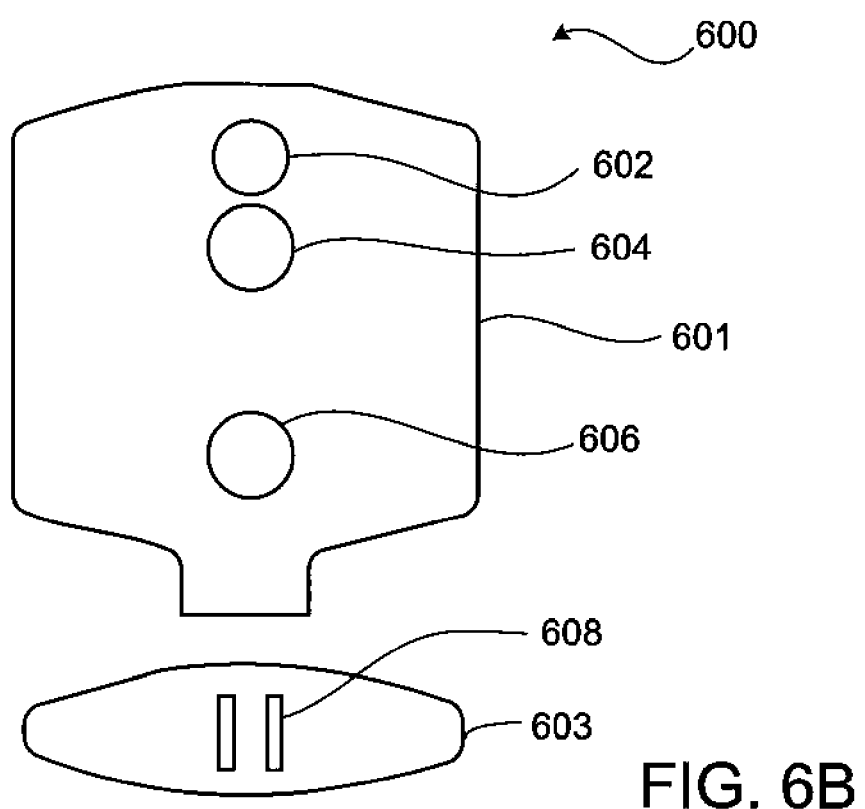
FIG. 6B is a schematic top view of an alternative embodiment of the light shield of FIG. 6A.

Referring to FIGS. 6A and 6B, the probe head 400 can be located in proper position by a light shield 600. Light shield 600 has an opening 602 through which a foot 520 of probe 400 fits, an opening 604 though which illumination light port 506 fits, and an opening 606 through which a second foot 520 fits. The second foot can house illumination light port 514 fit and detection light port 508. Thus, the light shield locates the feet 520 and the illumination and detection light ports 506, 514, and 508 of probe head 400 in a fixed position. Light shield 600 includes an opaque material that shields the patient's body from stray light, such that only light from illumination light ports 506 and/or 514 reaches the patient, and such that light collected in detection light port 508 is due only to light having a known spectrum that emerges from illumination light port 506. Light shield 600 can extend about 3.5 cm in all directions from the detection light port 508 to shield the detection port from stray light. With probe head 400 positioned in the light shield 600, the probe head can be positioned against the patient's body, for example, by taping, strapping, or sticking the light shield against the patient's body. For example, probe head 400 can be held against light shield 600 with double-sided adhesive, which allows probe head 400 to contact the patient's skin without excessive pressure that could alter the blood volume under the probe head.

As shown in FIG. 6A, in some embodiments, the light shield can be made in one piece having a main part 601 that has the various openings or apertures, and a cable management part 603 connected to the main part 601 by a narrow connecting region 605. In other embodiments, as shown in FIG. 6B, the light shield has a two-piece design in which the cable management part 603 is separate from the main upper part 601. This arrangement enables the two parts to be separated by a distance greater than the length of connecting region 605. In many of these embodiments, the light shield cable management part 603 typically includes a clip 608 or other mechanism that can secure a cable that contains the fiber bundles 116a, 116c, and 116d that transport light between spectrometer unit 502 and probe head 400. Clip 608 secures the cable, so that the weight of the cable does not displace the probe head from its location on a patient. The shield 600 can be made from plastic, for example, or from another lightweight opaque material. The light shield can also be made from a thermally-conductive material, such as a thin sheet of copper or aluminum to assist in the dissipation of excess heat, so that the heat is not transferred to the patient's skin.

Optical Bench and Shutter System

The optical bench can include a shutter system 110 for directing the light to different legs of the fiber optic cable system. By controlling the path of the light in the cable system, the shutter system can be used to selectively illuminate the sample with different illumination fibers 116a or 116d.

Figure 7:
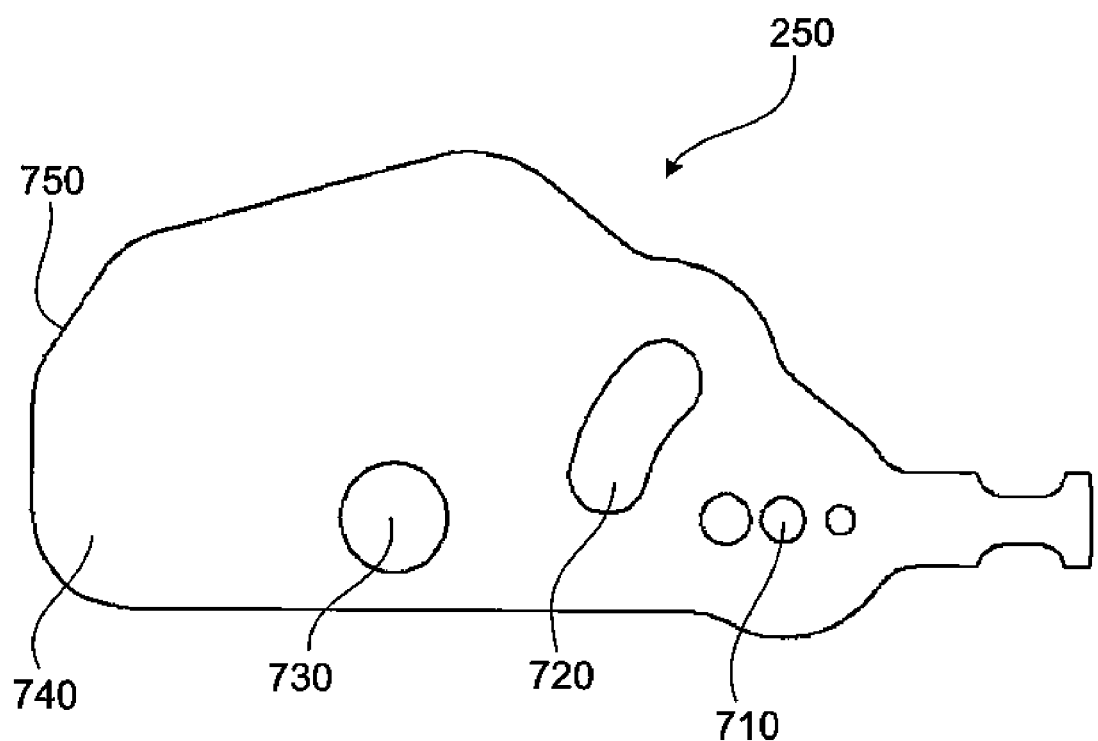
FIG. 7 is a schematic view of a shutter used in the spectrometer system of FIG. 1.

Referring again to FIG. 2, optical bench 108 provides a mount for a stepper-motor 240 that actuates optical shutter 250 of the shutter system 110. Shutter 250 is positioned between lamp 104 and two fiber optic cables 116a and 116d, and is shaped such that it can either block or pass light to each of the two fiber optic cables. In FIG. 2, only the top edge of the shutter 250 is shown. A profile of opaque shutter 250 is shown in FIG. 7. Shutter 250 is coupled to stepper motor 240 by a shaft that passes through a hole 710 in the shutter. When the shaft rotates, the shutter is rotated about an axis passing through the center of the hole 710. A second shaft (not shown) fixed to the optical bench 108 passes through a second hole 720 in shutter 250 and limits the rotational motion of shutter 250.

When shutter 250 is rotated maximally in the clockwise direction, as shown in FIG. 7, hole 730 in the shutter is located between lamp 104 and fiber optic cable 116a that leads to sample 102, so that light propagates through hole 730 and sample 102 is illuminated by light emerging from fiber bundle 116a. With shutter 250 in this position, light reflected from sample 102 is collected by cable 116c and guided to spectrograph 114. In this position, end 740 of shutter 250 blocks light from entering cable 116d.

When shutter 250 is rotated counterclockwise to a middle position, such that the shaft passing through hole 720 is positioned in the middle of hole 720, hole 730 is rotated out of the beam path of the light emitted from lamp 104. Thus, light does not pass through hole 730, and is blocked by opaque shutter 250 from entering the sample cable 116a. Light is also blocked from entering the fiber bundle 116d by end 740 of shutter 250.

When shutter 250 is rotated maximally in the counterclockwise direction, light does not pass through hole 720 and is blocked by the opaque shutter from entering sample cable 116a. Light passes over angled edge 750 of shutter 250 and enters fiber bundle 116d and reaches spectrograph 114. In this position, spectrograph 114 measures a reflectance spectrum of sample 102 when the sample is illuminated by fiber bundle 116d.

Figure 8:
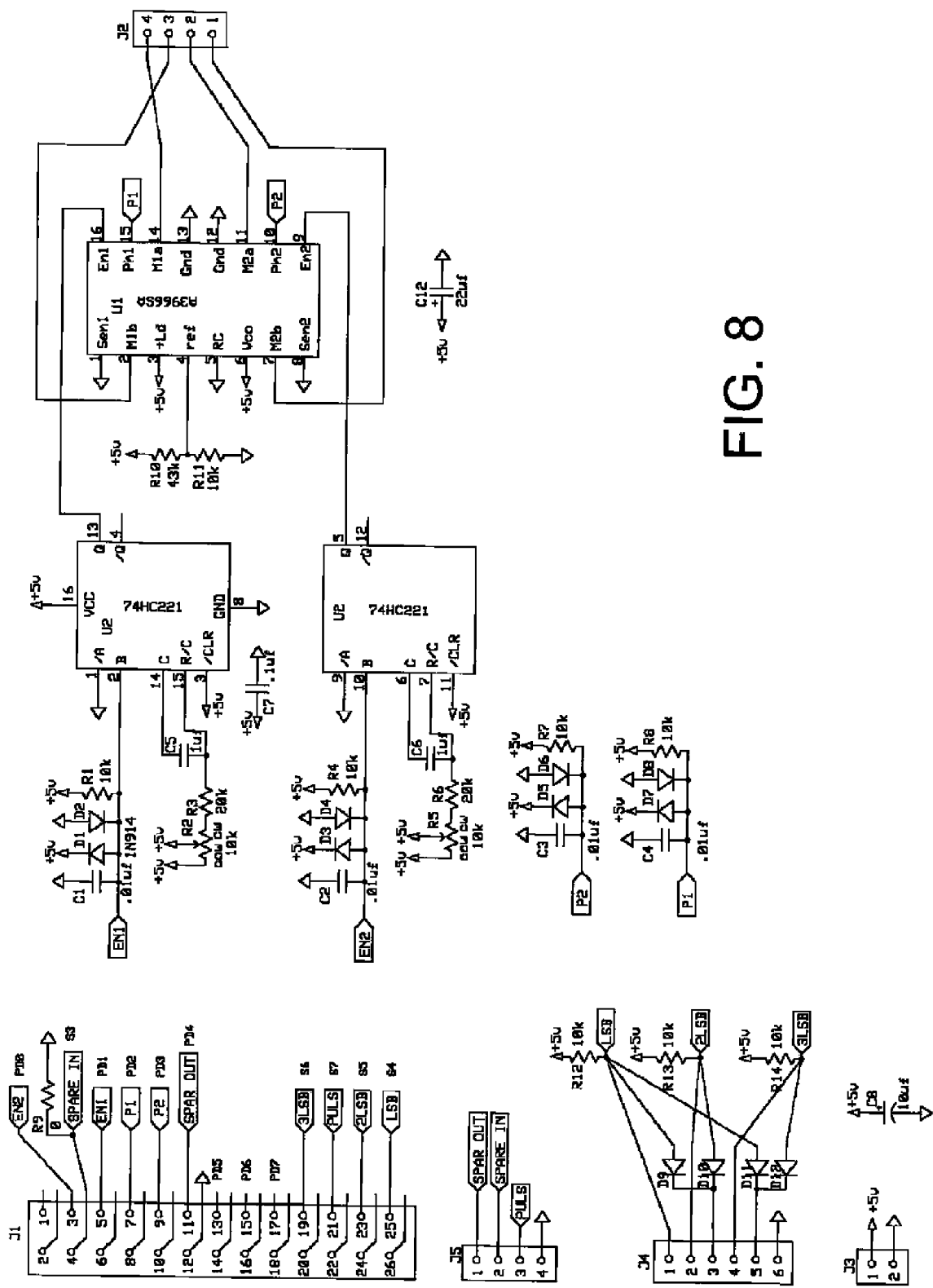
FIG. 8 is a circuit diagram of an electrical circuit for controlling the shutter shown in FIG. 7.
Figure 9A:
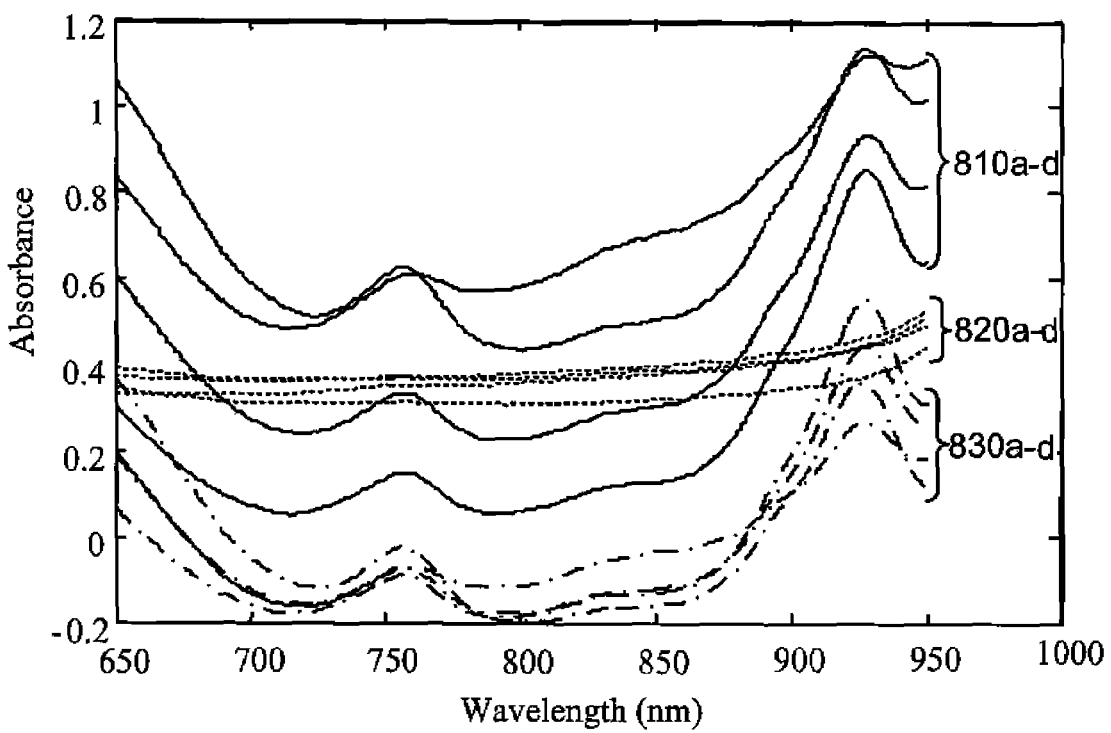
FIGS. 9A-9E are graphs that show results of a correction to remove spectral interference due to overlying layers from reflectance spectra measured from a human subject.
Figure 9B:
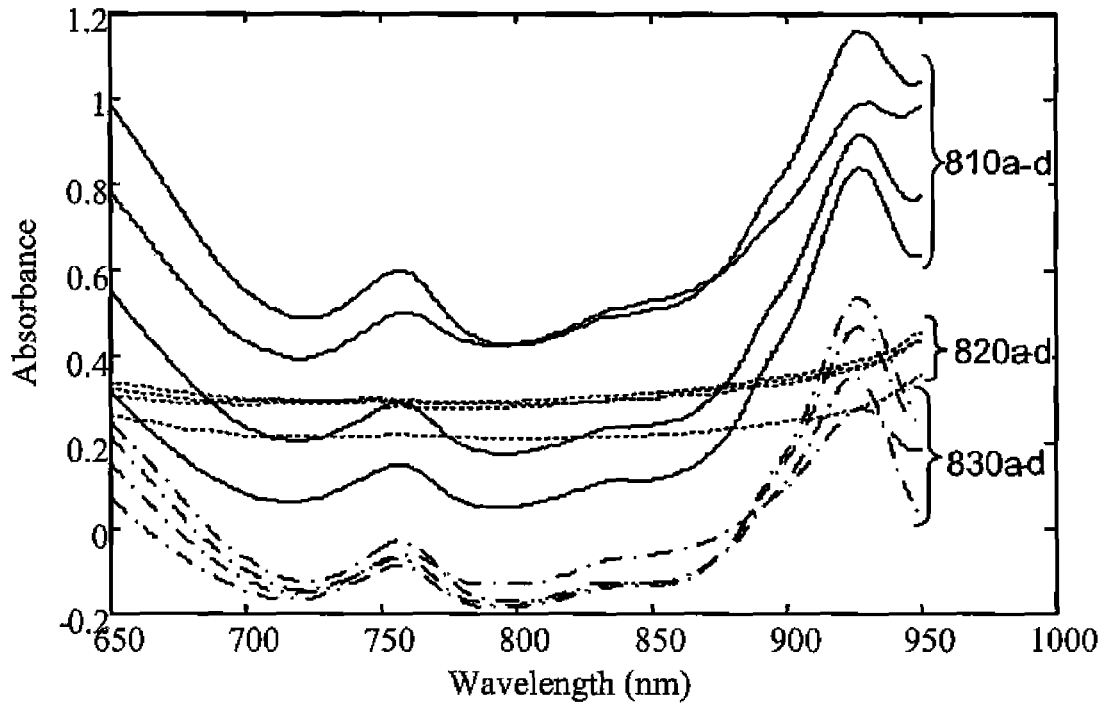
Figure 9C:
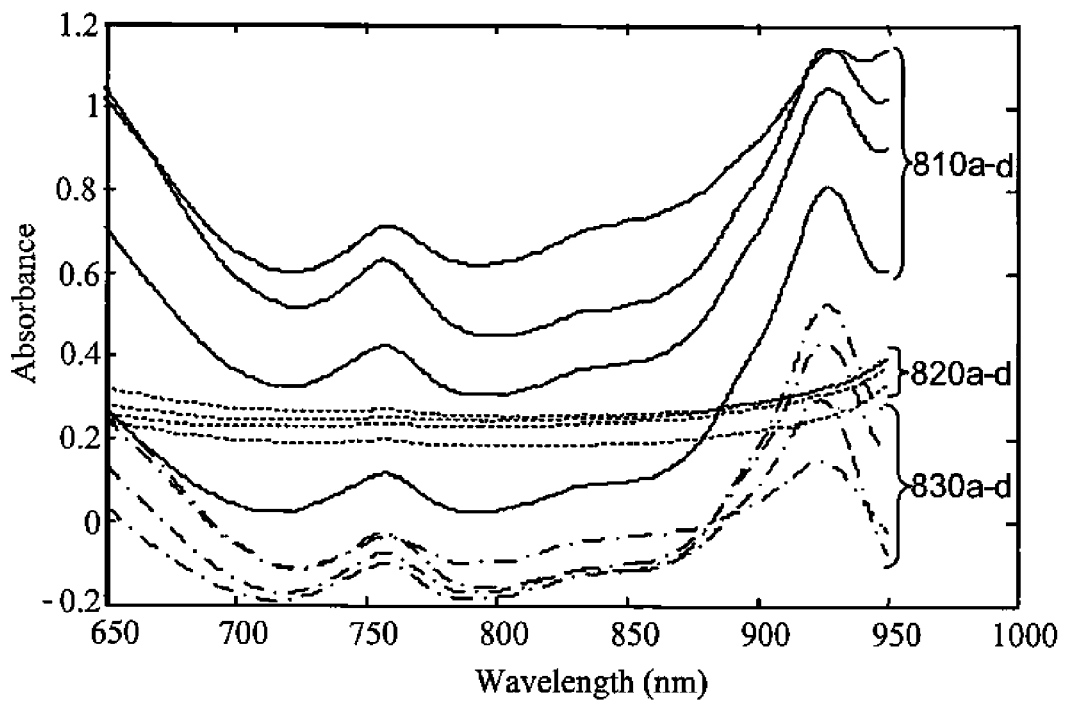
Figure 9D:
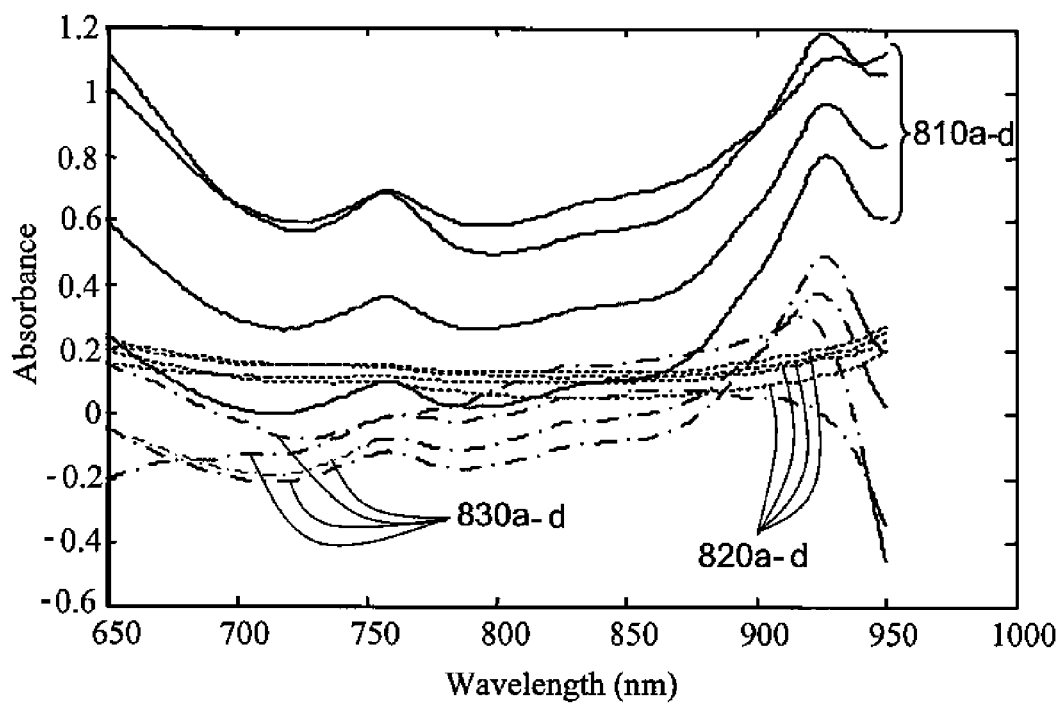
Figure 9E:
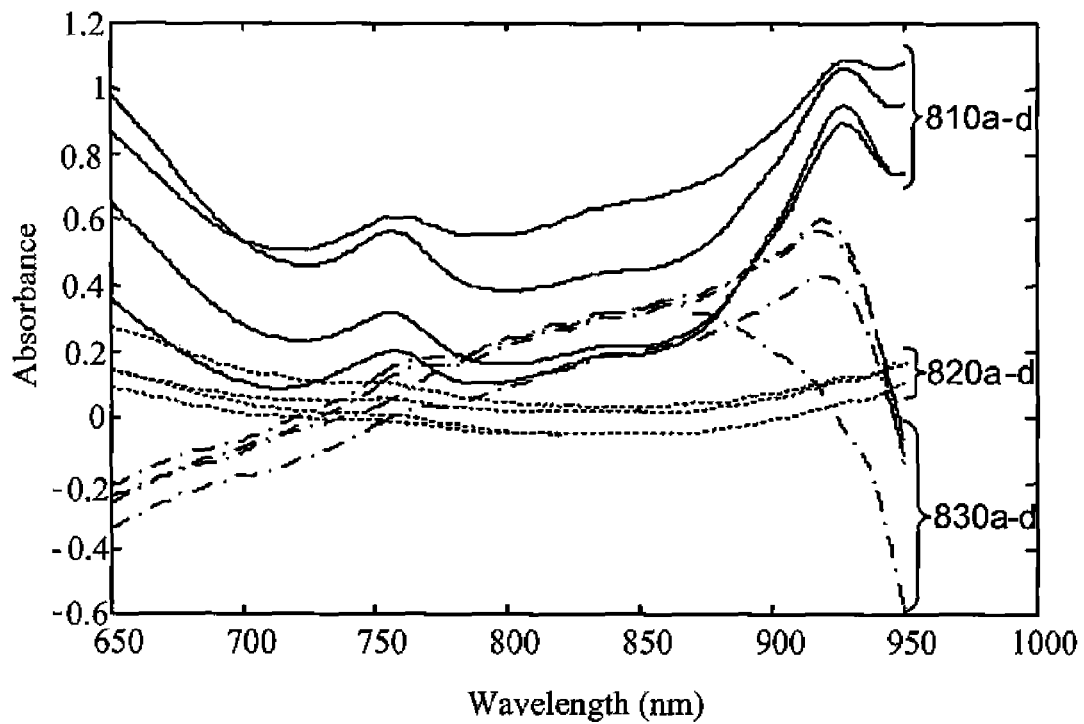
Figure 10A:
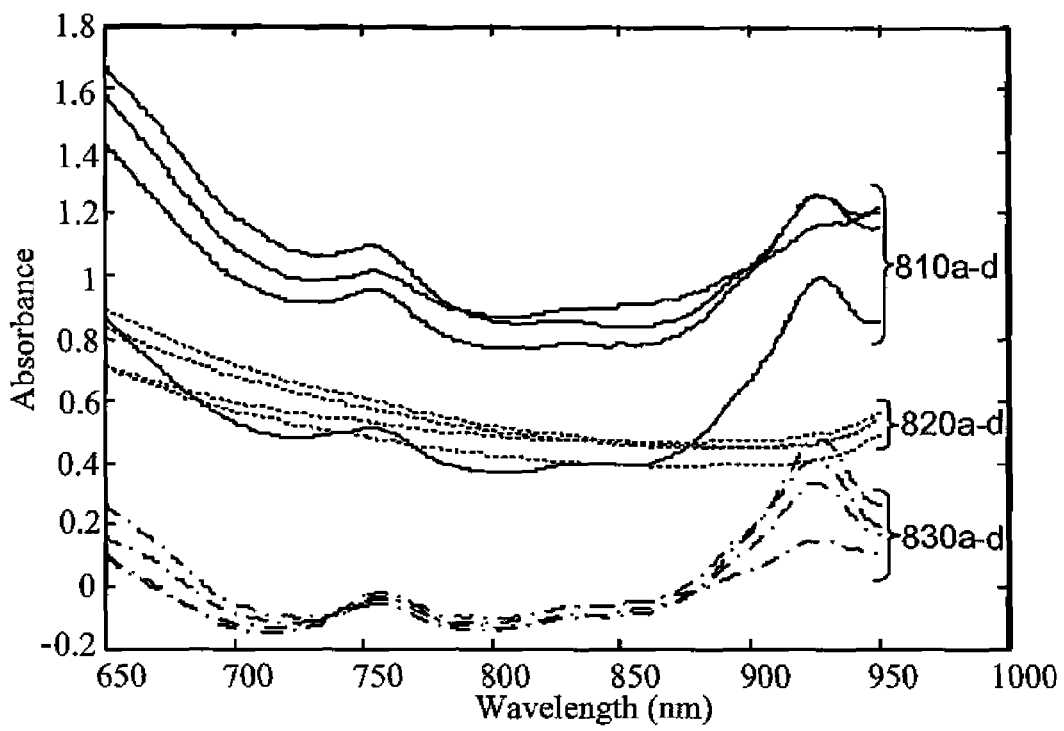
FIGS. 10A-10E are graphs that show results of a correction to remove spectral interference due to overlying layers from reflectance spectra measured from another human subject.
Figure 10B:
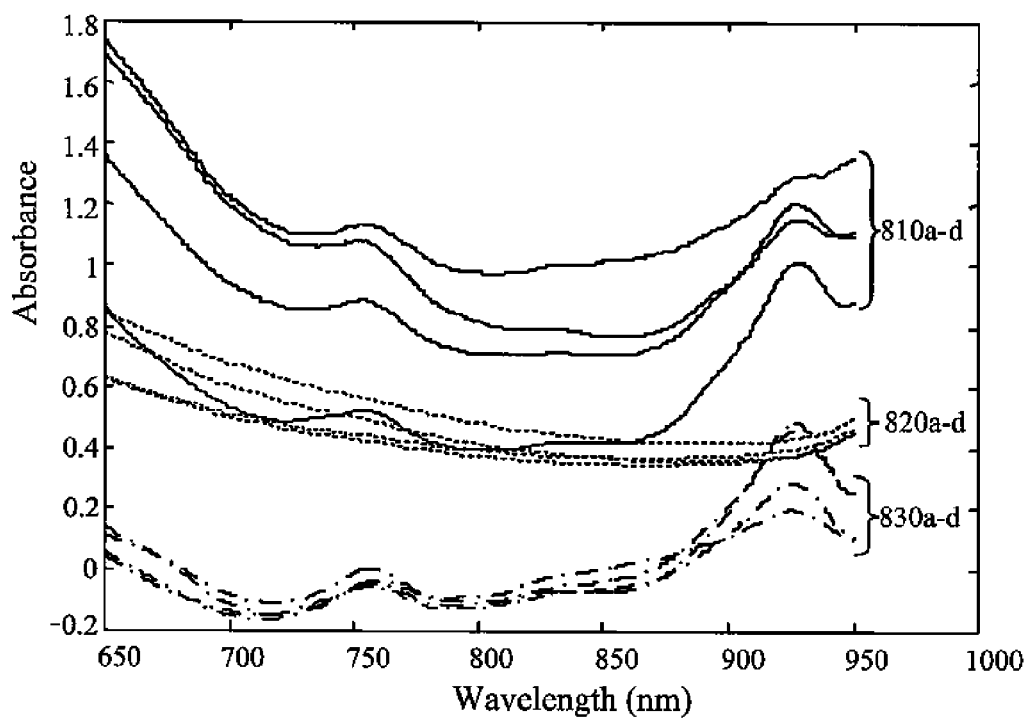
Figure 10C:
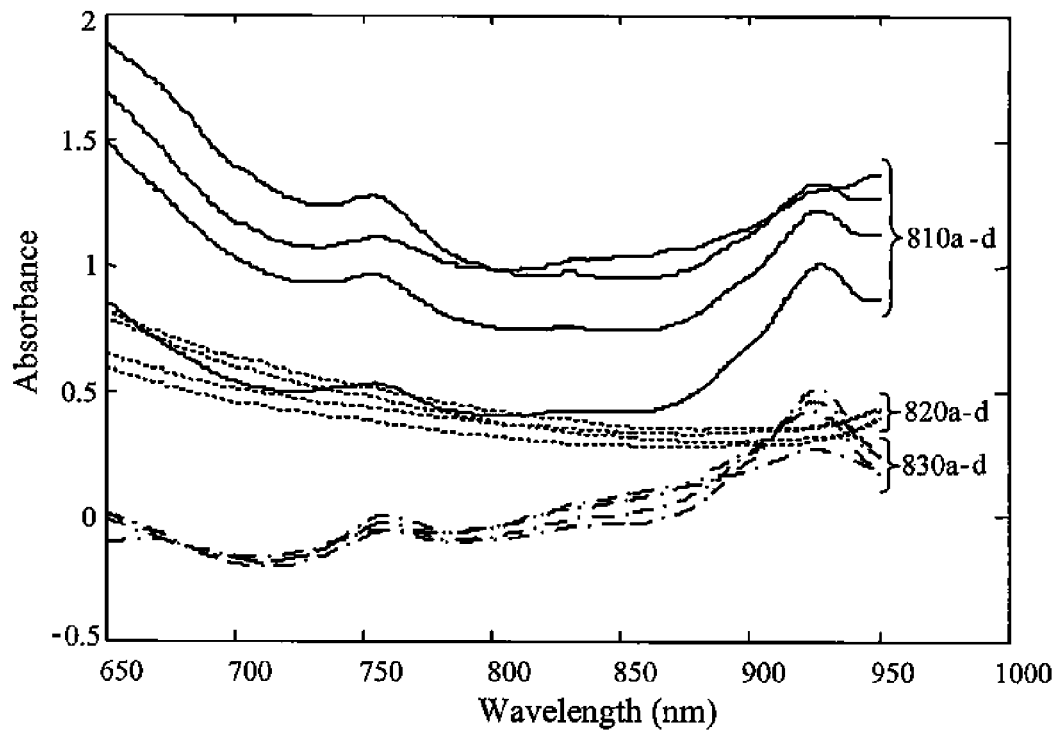
Figure 10D:
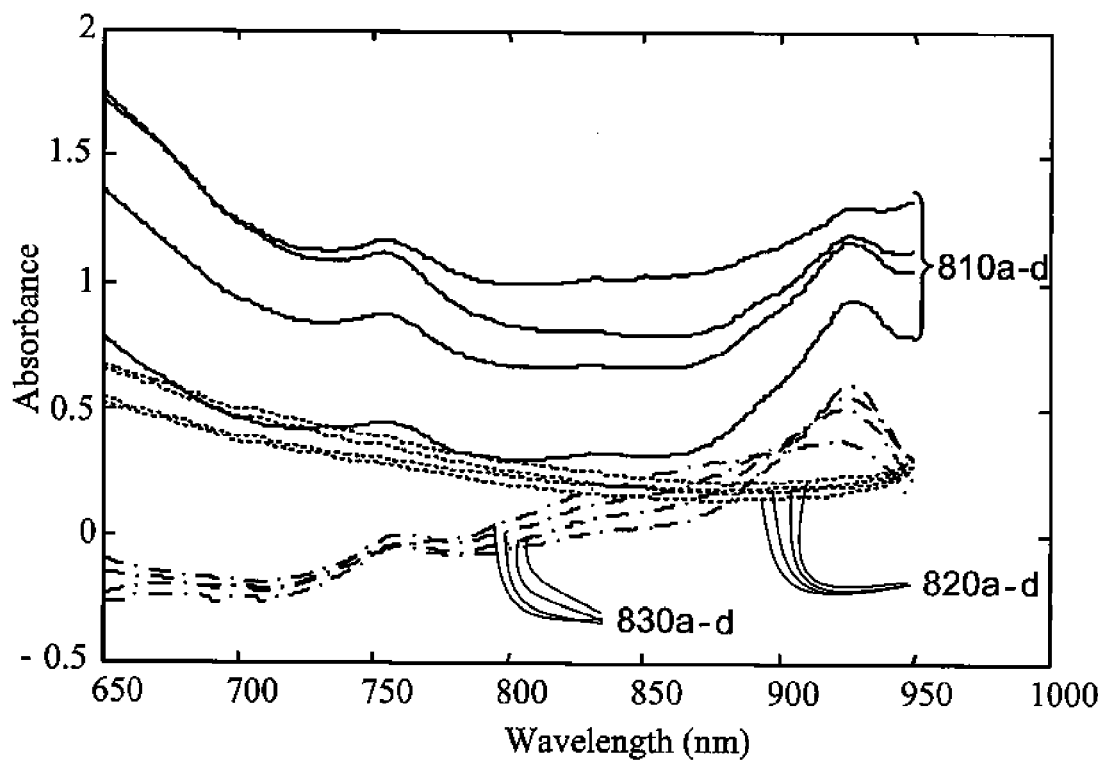
Figure 10E:
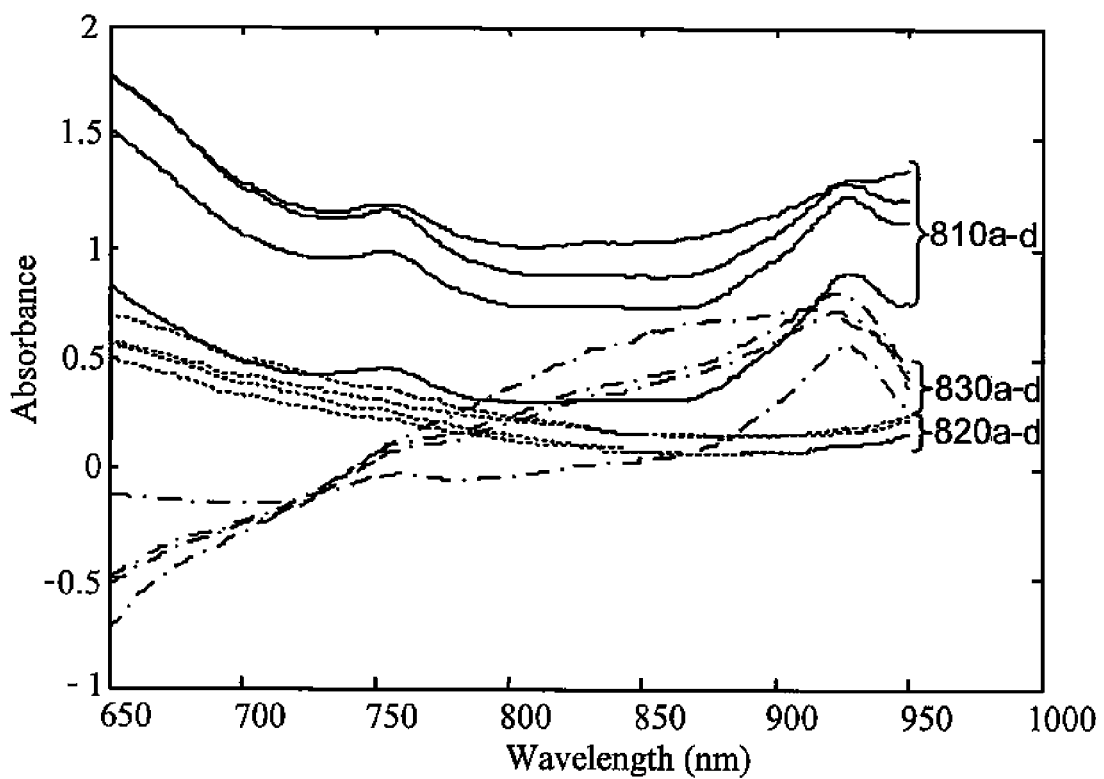

Computer 118 controls shutter 250 to switch data acquisition in spectrograph 114 between collecting data in a first channel (i.e., when sample 102 is illuminated with light from fiber bundle 116a) and collecting data in a second channel (i.e., when sample 102 is illuminated with light from fiber bundle 116d). Computer 118 can control shutter 250 via a shutter driver circuit. One embodiment of a suitable shutter driver circuit is shown in FIG. 8. The operation of this circuit is described in U.S. application Ser. No. 11/113,347 entitled "SPECTROMETER SYSTEM FOR OPTICAL REFLECTANCE MEASUREMENTS", filed Apr. 25, 2005, and now published as U.S. Publication Number 2005/0259254, the entire contents of which are incorporated herein by reference.

Computer 118 also controls how spectrograph 114 collects data. For example, computer 118 can control an integration time of the spectrograph detector, a number of spectra to be averaged, and an amount of smoothing before spectra are stored in the computer. It is possible for computer 118 to do this independently for each channel of data acquisition. Parameters can be chosen to maximize a response in each of the reference channel and the sample channel without saturating the detector.

Other Spectrometer Systems

Suitable light sources for spectrometer system 100 include incandescent sources, e.g., lamps, light emitting diodes (LEDs), laser-based sources, and other sources. For example, one or more LEDs can be combined to provide light for use in making reflectance measurements from a sample. The light provided by the various light sources can include wavelengths in selected regions of the electromagnetic spectrum such as the infrared and/or near-infrared region, the visible region, the ultraviolet region, and/or other regions of the electromagnetic spectrum, for example.

In some embodiments, spectrometer system 100 may be configured to illuminate a sample directly, without coupling illumination light from a light source through a fiber optic cable. For example, the light source can be an incandescent lamp positioned to directly illuminate a sample through an illumination port such as an aperture. Light reflected from the sample can then be received by one or more detectors and analyzed.

In certain embodiments, more than one detector can be used. For example, light can be used to illuminate a sample from an illumination port, and illumination light reflected from the sample can be received in two detection ports. Each of the two detection ports can be coupled to a spectrometer configured to measure a spectrum of the reflected light, so that the detection system includes two spectrometers operating in parallel. Spectral data can be acquired simultaneously at each detection port, which can provide a speed advantage relative to systems that have only a single spectrometer. The system can operate without use of a shutter system for blocking and unblocking illumination ports, which can reduce the cost of the system and increase the system's mechanical reliability.

Spectral Correction Algorithms

There are three different correction algorithms that can be implemented. Although each correction algorithm works well individually, any two algorithms, or all three algorithms, can be used together to correct measured spectral data.

1. Short-Distance Corrections

Spectral contributions that arise from tissue layers overlying tissue layers of interest (e.g., underlying tissues) can be corrected by subtracting the contributions due to the overlying layers from reflectance spectra that include contributions from both the overlying and underlying layers. Reflectance spectra that include contributions from both types of layers, and reflectance spectra that include contributions from substantially only overlying layers, can be measured separately using spectrometer system 100. For example, as shown in FIG. 5, the distance $(SD)_2$ between illumination port 506 and detection light port 508 is greater than the distance $(SD)_1$ between illumination port 514 and detection light port 508. The distance $(SD)_2$ can be selected such that reflectance spectra $R_{sfm}$ recorded when sample 102 is illuminated with light from illumination port 506 contain spectral information about skin layer 102s, fat layer 102f, and muscle layer 102m. The distance $(SD)_1$ can be selected such that reflectance spectra, $R_{sf}$ recorded when sample 102 is illuminated with light from illumination port 514, substantially contain spectral information only about skin layer 102s and fat layer 102f. The instrument parameters, fiber size, and spectrometer integration time of system 100 can be chosen to obtain a high signal-to-noise ratio in the reflectance spectra for the dynamic range of the system for each illumination port and detection port.

Before subtracting out spectral information contained in the $R_{sf}$ spectra that is due to overlying layers from the spectrum $R_{sfm}$ that includes information about both the overlying and underlying tissue layers, the $R_{sf}$ spectra can be normalized to the $R_{sfm}$ spectra, so that the spectra share a common measurement space. To transform $R_{sf}$ into the measurement space of $R_{sfm}$, a photometric mapping of the $R_{sf}$ spectra to the $R_{sfm}$ spectra is performed. First, reflectance spectra are recorded from three or more optically homogenous reflectance standards having reflectivity values ranging from 2% to 99% when light is incident on sample 102 from illumination port 506 and from illumination port 514. Next, the reflectance spectrum for each reference standard is estimated by dividing each measured intensity spectrum by the spectrum recorded for the 99% reference standard. For example, the estimated reflectance, R, of the 50% standard is 50/99 (i.e., 50.5%). Likewise, the estimated reflectance of the 99% standard is 99/99 (i.e., 100%). Finally, a wavelength-specific polynomial model correlating spectra, $R_{sf}$, recorded when the standard is illuminated with light from second light port 514 with spectra, $R_{sfm}$, recorded when the standard is illuminated with light from first light port 506. Each wavelength-specific model is used to adjust the scale of the reflectance estimates from $R_{sf}$ to $R_{sfm}$. This procedure corrects for differences in light throughput and collection efficiency when the different illumination ports 506 and 514 are used. The polynomial model can be implemented as follows:

$$R_{sfm}(n, \lambda) = aR_{sf}(n, \lambda)^2 + bR_{sf}(n, \lambda) + c \quad (1)$$

where n and $\lambda$ are indices representing the target reflectance values (2-99%) and the light wavelength, respectively, and a, b, and c are wavelength-specific polynomial coefficients. The polynomial coefficients allow a mapping of future measurements of tissue spectra, $R_{sf}$, to spectra, $\tilde{R}_{sf}$, that are normalized to the $R_{sfm}$ spectra. Equation 1 describes a second order polynomial model. In general, however, polynomial models of higher order (e.g., third order, fourth order, and even higher order) can be implemented.

After normalization of the spectra recorded with light from the two different illumination light ports 506 and 514, the spectra recorded with the different illumination light locations are orthogonalized (i.e., the spectral components due to the overlying layers are removed from the spectra that include components that are due to both the overlying and underlying layers. Orthogonalization involves matrix multiplication. First, a wavelength dependent weight, w, indicative of a correlation between the spectra $R_{sf}$ and $R_{sfm}$ is determined from the following equation:

$$w = R_{sfm}^T \tilde{R}_{sf} (\tilde{R}_{sf}^T \tilde{R}_{sf})^{-1} \quad (2)$$

where the superscript T indicates the transpose of a matrix, and $\tilde{R}_{sf}$ is a vector that corresponds to a spectrum of reflected light recorded when light is incident on sample 102 from illumination port 514 and then photometrically mapped onto the measurement space of $R_{sfm}$. After the weight is determined, the spectral features of the overlying layers can be removed by using the following equation:

$$\hat{R}_{ort} = R_{sfm} - \tilde{R}_{sf} w^T \quad (3)$$

where $\hat{R}_{ort}$ is an orthogonalized spectrum that results after the reflectance components due to skin and fat are removed, and that substantially includes only information from the underlying (muscle) layer 102m. $\hat{R}_{ort}$ can be used with PLS or other multivariate calibration techniques to develop calibration equations for determining chemical properties of the underlying layer 102m from the orthogonalized reflectance spectrum, $\hat{R}_{ort}$, where the calibration equations are independent of the optical effects of overlying layers.

When the calibration equations are used in a medical monitoring device, patient spectra can be collected with a fiber optic probe of the same design as used to generate the calibration equations, and the orthogonalized spectrum should be calculated before it is used in the calibration equation.

2. Correction by Standard Normal Variate Scaling

Standard normal variate (SNV) scaling techniques can be used to reduce scatter and other undesired contributions to measured reflectance spectra. Suitable SNV implementations are disclosed, for example, in R. J. Barnes et al., *Applied Spectroscopy* 43, 772 (1989), the entire contents of which are incorporated herein by reference. SNV methods can be used, for example, to reduce contributions to measured reflectance spectra that arise from variations in optical properties of tissues of interest, such as muscle tissues.

3. Correction by Principal Component Analysis Loading

In some embodiments, spectral reflectance measurements are recorded from multiple locations on a subject's body, and/or from multiple subjects. Variations in optical properties of tissues of interest from one subject to another, for example, can introduce variations into the reflectance data that are unrelated to measurement analytes of interest. For example, in muscle tissue reflectance spectra recorded from a set of subjects, a measurement analyte of interest may be muscle tissue pH. However, in addition to variations that arise due to changes in muscle tissue pH, reflectance spectra recorded from muscle tissues in different subjects can also include spectral contributions that arise from variations in muscle tissue texture, and/or capillary density, and/or fiber structure, and/or other structural properties of the muscle tissues in the different subjects. These variations in structural properties typically produce variations in wavelength-dependent scattering coefficients for the muscle tissues in the different subjects.

A large set of subjects may be used to model optical property variations in tissues of interest. However, the time and expense associated with measuring and analyzing reflectance spectra from a large set of test subjects may make this approach impractical for clinical applications. Alternatively, numerical algorithms can be used to reduce and/or remove spectral contributions in reflectance spectra that arise from optical property variations in tissues of interest, prior to using the reflectance spectral data in PLS modeling applications to measure analytes of interest.

Principal component analysis (PCA) loading corrections can be used to reduce and/or remove contributions to reflectance spectra that arise from analyte-irrelevant variations in optical properties of tissues of interest (e.g., tissues in which analytes of interest are measured). Optical properties that exhibit such variations can include scattering properties, absorption properties, tissue refractive indices, and other properties. In general, variations in infrared absorption by tissues of interest are also related to concentrations of one or more analytes of interest. Accurate measurement of analytes of interest may therefore include determining and correcting for the analyte-irrelevant contributions to reflectance spectra.

PCA analysis can be used to obtain spectral "signatures" of the analyte-irrelevant variations, which can then be removed from the spectral reflectance data via orthogonalization steps. PCA loading corrections can be applied during both calibration and predictive steps to further improve PLS models constructed from the corrected spectral reflectance data.

Variations in spectral reflectance measurements that arise from variations in optical properties of tissues of interest can be reduced and/or removed in a series of steps. For example, in some embodiments, a first analysis step includes determining variations in spectral reflectance data that are not relevant to a target analyte by PCA on a set of spectra collected from different subjects (and/or from different locations on the same subject) in the same calibration set with substantially similar values of the analyte. The variations can be expressed as a set of loading vectors of principal spectral components obtained from PCA. The first analysis step is described by Equation 4:

$$X_{0,mc} = X_0 - X_{0,mean} = SP^T + E \quad (4)$$

In Equation 4, $X_0$ is a matrix with dimensions $m_0 \times n$. Each of the $m_0$ rows of $X_0$ corresponds to a reflectance spectrum recorded for a different sample used for PCA, and n is the number of wavelength points in each reflectance spectrum. The spectra in $X_0$ include analyte-irrelevant spectral reflectance variations. Matrix $X_{0,mean}$ has dimensions $m_0 \times n$ and includes $m_0$ rows, where each row is a $1 \times n$ vector whose elements correspond to the column mean values of $X_0$, so that subtracting $X_{0,mean}$ from $X_0$ yields matrix $X_{0,mc}$ with dimensions $m_0 \times n$, where $X_{0,mc}$ is a mean-centered matrix of $X_0$. S is a PCA score matrix with dimensions $m_0 \times f_0$, where $f_0$ is a number of principal components used to model variations in $X_0$. Matrix P is the PCA loadings matrix and has dimensions $n \times f_0$. Matrix E, with dimensions $m_0 \times n$, is a matrix of spectral residuals of $X_0$ that are not modeled by PCA.

In a second analysis step, spectra used for PLS calibration and spectra used for PLS-based prediction are orthogonalized with respect to the loading vectors of the principal components obtained in the first step. Spectral contributions due to variations in optical properties of the tissues of interest are reduced and/or removed in the corrected spectra which result from the second analysis step. The second analysis step is described by Equation 5:

$$X_{ort} = (X - X_{0,mean(m,n)}) - (X - X_{0,mean(m,n)})P_1 P_1^T + X_{0,mean(m,n)} = X - (X - X_{0,mean(m,n)})P_1 P_1^T \quad (5)$$

In Equation 5, $X_{ort}$ is the orthogonalized (e.g., corrected) spectral matrix with dimensions $m \times n$, where m is the number of samples, e.g., the m rows of $X_{ort}$ correspond to corrected reflectance spectra recorded from m different samples. Matrix X with dimensions $m \times n$ corresponds to m original, uncorrected spectra. Matrix $X_{0,mean(m,n)}$ with dimensions $m \times n$ includes m rows, where each row is a $1 \times n$ vector whose elements correspond to the column mean values of $X_0$. $P_1$, with dimensions $n \times f_1$, is a truncated loadings matrix, where the number of columns $f_1$ is equal to a number of orthogonalization factors used in the orthogonalization procedure. In general, $f_1$ is less than or equal to $f_0$, and a value for $f_1$ is selected on the basis of the element values in the S and P matrices calculated in Equation 4. Following orthogonalization, the corrected reflectance spectra in matrix $X_{ort}$ can be used in PLS calibration and/or modeling to predict values of analytes of interest.

4. Combined Correction Methods

In certain embodiments, any two or all three of the short-distance methods, SNV methods, and PCA loading methods can be combined to correct reflectance spectra by removing spectral features that do not arise from measurement analytes of interest. For example, in some embodiments, short-distance correction methods can be applied first to a set of reflectance measurements to correct for spectral features due to tissue layers that overlie tissue layers of interest. SNV and PCA loading corrections can then be applied to the short-distance-corrected spectra in succession to correct for variations in optical properties in the tissue layers of interest, e.g., where the set of reflectance measurements includes reflectance data measured at different locations on a subject's body, and/or reflectance data from different subjects.

In general, the algorithms disclosed herein can be applied in a desired order to correct spectral reflectance data. The suitability of one or more correction algorithms applied in a selected order to reflectance data is typically assessed by determining the accuracy of a PLS model for an analyte of interest that is developed based on the corrected spectral reflectance data (discussed in more detail in the Examples).

Implementation

The equations and algorithms described above can be easily implemented in hardware or in software, or in a combination of both. The invention can be implemented in computer programs using standard programming techniques following the method steps and figures disclosed herein. The programs can be designed to execute on programmable processors or computers, e.g., microcomputers, each including at least one processor, at least one data storage system (including volatile and non-volatile memory and/or storage elements), at least one input device, such as a keyboard or push button array, and at least one output device, such as a CRT, LCD, or printer. Program code is applied to input data to perform the functions described herein. The output information is applied to one or more output devices such as a printer, or a CRT or other monitor, or a web page on a computer monitor with access to a website, e.g., for remote monitoring.

Each program used in the new system is preferably implemented in a high level procedural or object oriented programming language to communicate with a computer system. However, the programs can be implemented in assembly or machine language, if desired. In any case, the language can be a compiled or interpreted language.

Each such computer program can be stored on a storage medium or device (e.g., ROM or magnetic diskette) readable by a general or special purpose programmable computer, for configuring and operating the computer when the storage medium or device is read by the computer to perform the procedures described herein. The system can also be considered to be implemented as a computer-readable storage medium, configured with a computer program, where the storage medium so configured causes a processor in the computer to operate in a specific and predefined manner to perform the functions described herein.

Although any communications network can be used to obtain results from remote monitoring, the Internet or wireless systems provide useful choices to transmit data.

EXAMPLES

Spectral Effects of Short-Distance Corrections

Example 1

Experiments were performed to determine an optimum distance $(SD)_1$ between the illumination probe 514 and detection probe 508 to correct for the presence of skin and fat over human muscle in an embodiment of system 100. A probe 400 with an adjustable short source-detector distance, $(SD)_1$, of 2 mm-6 mm and a fixed long source-detector distance, $(SD)_2$, of 32.5 mm was used to measure spectra from four different anatomical positions (arm, calf, shoulder, and thigh) having different fat layer thicknesses on four different subjects to determine which $(SD)_1$ distance would result in the lowest variation in measurements of an analyte for measurements performed on the different locations of the person. Ideally, the spectral differences caused by the different fat thicknesses from the different positions on a person should be corrected after the orthogonalization, i.e., all four spectra measured from different body parts of a person should overlap, because the same information should be recovered from a person's muscles regardless of what body part is measured. Moreover, the spectral difference caused by the skin color and different fat thickness on different people should be decreased, i.e., a better correlation between the spectra and the hematocrit ("Hct") values of patients should be obtained when the spectra are orthogonalized to remove spectral contributions from the overlying skin and fat layers.

Reflectance spectra were measured from the arm, calf, shoulder and thigh of four human subjects using a fixed $(SD)_2$ distance of 32.5 mm and five different $(SD)_1$ distances of 1.83 mm, 2.5 mm, 3.0 mm, 4.0 mm, and 5.4 mm. The actual fat thicknesses for the subjects were measured at different positions using ultrasound and are listed in Table 1 below. The thigh position chosen for this study was on top of the rectus femoris muscle (front thigh), where thicker fat was found than the position on top of the vastus lateralis muscle (side thigh). Each person's Hct level was measured via invasive blood testing, and the levels are listed in Table 2 below.

TABLE 1

|  | Arm (mm) | Calf (mm) | Shoulder (mm) | Thigh (mm) |
| --- | --- | --- | --- | --- |
| Subject A | 4.4 | 3.5 | 9.8 | 9.5 |
| Subject B | 1.8 | 5.8 | 9.0 | 10.7 |
| Subject C | 3.2 | 1.4 | 2.6 | 2.0 |
| Subject D | 6.3 | 9.5 | 11.6 | 18.6 |

TABLE 2

| Subject A | 41.5% |
| --- | --- |
| Subject B | 44.8% |
| Subject C | 43.4% |
| Subject D | 40.8% |

FIGS. 9A-9E show the effects of short-distance corrections for overlying tissue layers on the spectra recorded from a Subject A for different $(SD)_1$ distances. The results in FIGS. 9A, 9B, 9C, 9D, and 9E were obtained for $(SD)_1$ distances of 1.83 mm, 2.5 mm, 3.0 mm, 4.0 mm, and 5.4 mm, respectively. In each figure, spectra 810 are $R_{sfm}$ spectra obtained when different parts of the subject's body were illuminated with light from illumination port 506, spectra 820 are $R_{sf}$ spectra obtained when different parts of the subject's body were illuminated with light from illumination port 514, and spectra 830 are orthogonalized spectra.

Differences among spectra recorded at different positions on a subject's body appear generally as baseline shifts caused by the different fat thicknesses, and are decreased by the orthogonalization process. Corrected spectra 830 are closer together than raw spectra 810. For probes having $(SD)_1$ distances of 1.83 mm, 2.5 mm, and 3.0 mm, the orthogonalized spectra are closer together and their shapes are unchanged compared to the raw spectra. For probes having $(SD)_1$ distances of 4.0 mm and 5.4 mm, the spectra are closer together after correction, and certain features of the spectra are changed. For example, the absorption peak due to hemoglobin (Hb) at 760 nm is less pronounced after orthogonalization at $(SD)_1$ distances of 4.0 mm and 5.4 mm. This may imply that certain useful information from the muscle layer (where significant Hb absorption occurs) is diminished by the correction process. This is contrary to the objective of correcting for the influence of fat and skin layers, but keeping the muscle information. This effect may be due to deeper light penetration at large $(SD)_1$ distances. As light penetrates more deeply inside tissue, more information about the muscle layer is captured, and the correction between the short $(SD)_1$ distance and the long $(SD)_2$ distance may sacrifice some muscle information.

Similarly, FIGS. 10A-10E show correction results for spectra from the four body parts of a Subject C for different $(SD)_1$ distances. While Subject A had Caucasian skin and Subject C had Negroid skin, the results of the orthogonalization process are similar for both subjects. Absolute absorbance values of Subject A's and Subject C's skin are quite different, as evidenced by a comparison of spectra 820 in FIGS. 9A-9E with the spectra 820 in FIGS. 10A-10E. However, the corrected spectra for the two subjects, for which the spectral components due to the skin are subtracted out, are quite similar.

To examine correlations between corrected spectral reflectance data and Hct values, mean absorbance values of the spectra at the arm, calf, shoulder, and thigh of a subject were calculated for each subject, and a relationship between the subject's mean absorbance value and the corresponding subject Hct value was established for each $(SD)_1$ distance before and after short-distance corrections were applied to the reflectance spectra. A predominant hemoglobin feature in tissue absorption spectra is the deoxyhemoglobin peak at 760 nm, and the height of this peak in the spectra for each subject should be linearly related to the hematocrit level of the subject.

Table 3 shows the $R^2$ correlation values of the relationship between the mean absorbance at 760 nm for 4 different anatomical positions and the Hct values for the four different $(SD)_1$ distances (i.e., 1.83 mm, 2.5 mm, 3.0 mm, and 4.0 mm). From the values in Table 3, it can be seen that $R^2$ improved after the correction. This indicates that a strong correlation between the spectra and the Hct values is established by correcting the $(SD)_2$ distance spectra, $R_{sfm}$, against the $(SD)_1$ distance spectra, $R_{sf}$.

TABLE 3

| $(SD)_1$ Distance | Before | After |
| --- | --- | --- |
| 1.83 mm | 0.577 | 0.967 |
| 2.5 mm | 0.480 | 0.996 |
| 3.0 mm | 0.471 | 0.975 |
| 4.0 mm | 0.476 | 0.925 |

From the above results, an $(SD)_1$ distance of about 2.5 mm may provide optimal results for this embodiment. In general, the short source-detector distance can be determined through experiments as described above, or through Monte Carlo modeling, if the absorption and scattering coefficients of all the sample layers are known.

Example 2

Figure 11:
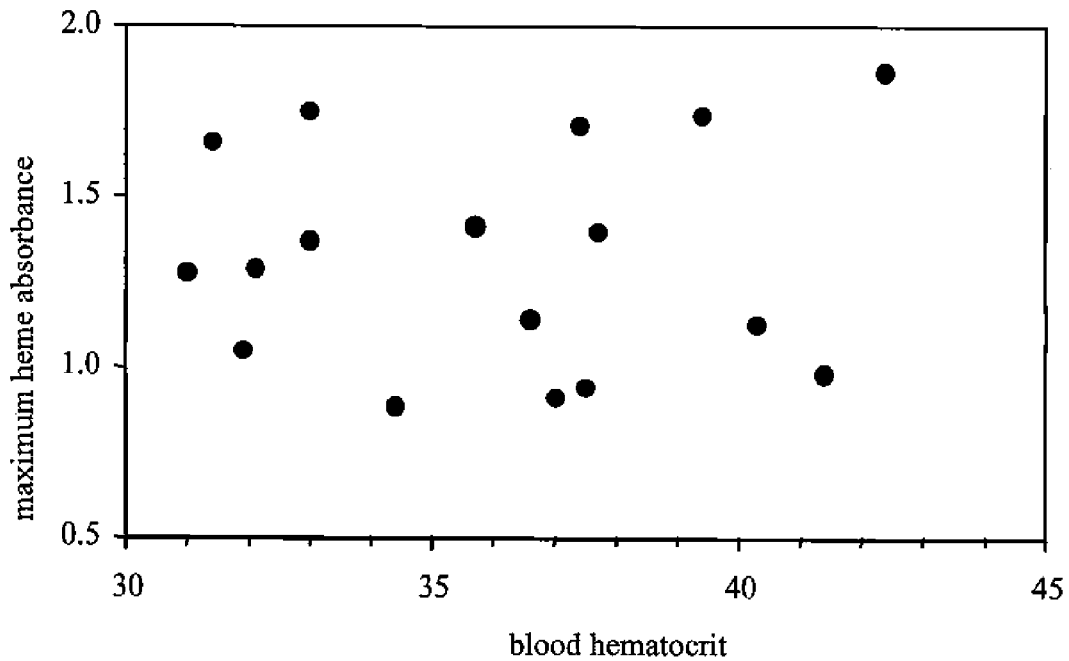
FIG. 11 is a graph showing values of maximum heme absorbance versus measured blood hematocrit for uncorrected spectral data.
Figure 12:
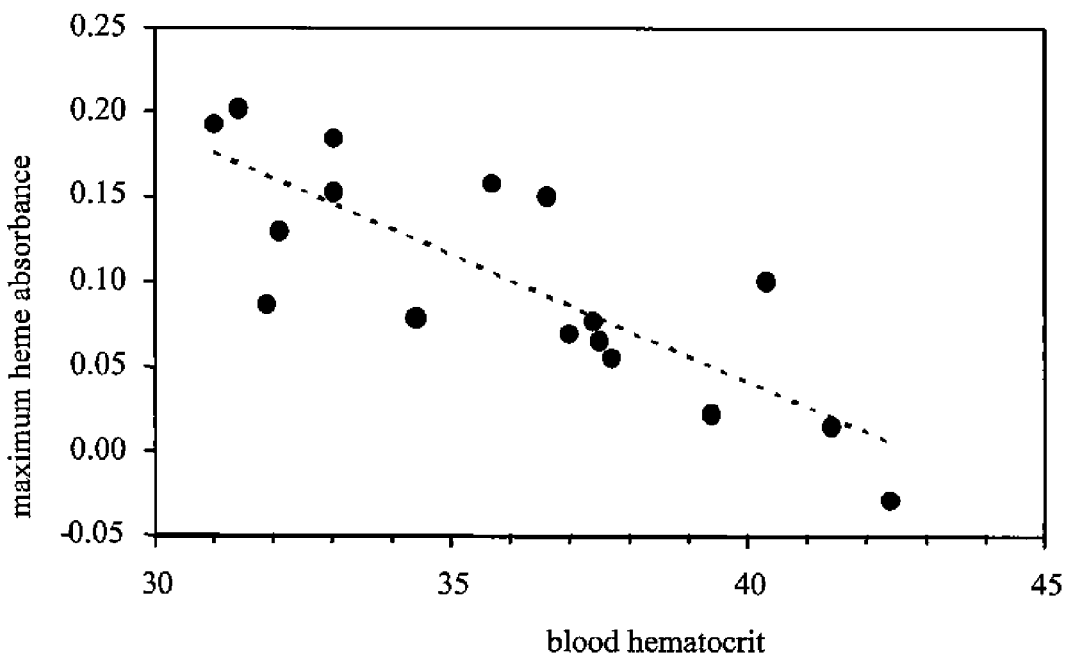
FIG. 12 is a graph showing values of maximum heme absorbance versus measured blood hematocrit for spectral data corrected for effects due to overlying skin and fat layers.

Another example of short-distance correction of reflectance spectra to improve correlations between measured spectral intensities and analytes of interest is shown in FIGS. 11 and 12. FIG. 11 shows a series of measurements of maximum heme absorption (including contributions from both hemoglobin and myoglobin) in 17 different human subjects. The spectral data from each subject was collected from the flexor digitorum profundus. The spectral data in FIG. 11 is uncorrected, and there is no strong correlation between maximum heme absorbance and blood hematocrit levels measured for each of the subjects.

FIG. 12 shows maximum heme absorbance versus blood hematocrit calculated from reflectance spectra after short-distance corrections were applied to the reflectance spectra to correct for overlying skin and fat layers in the 17 subjects. A stronger linear relationship is observed in the corrected data, suggesting that predictive models such as PLS models based on the corrected spectral data will more accurately estimate hematocrit levels in patients and other subjects.

Spectral Effects of PCA Loading Corrections

Example 3

Figure 13:
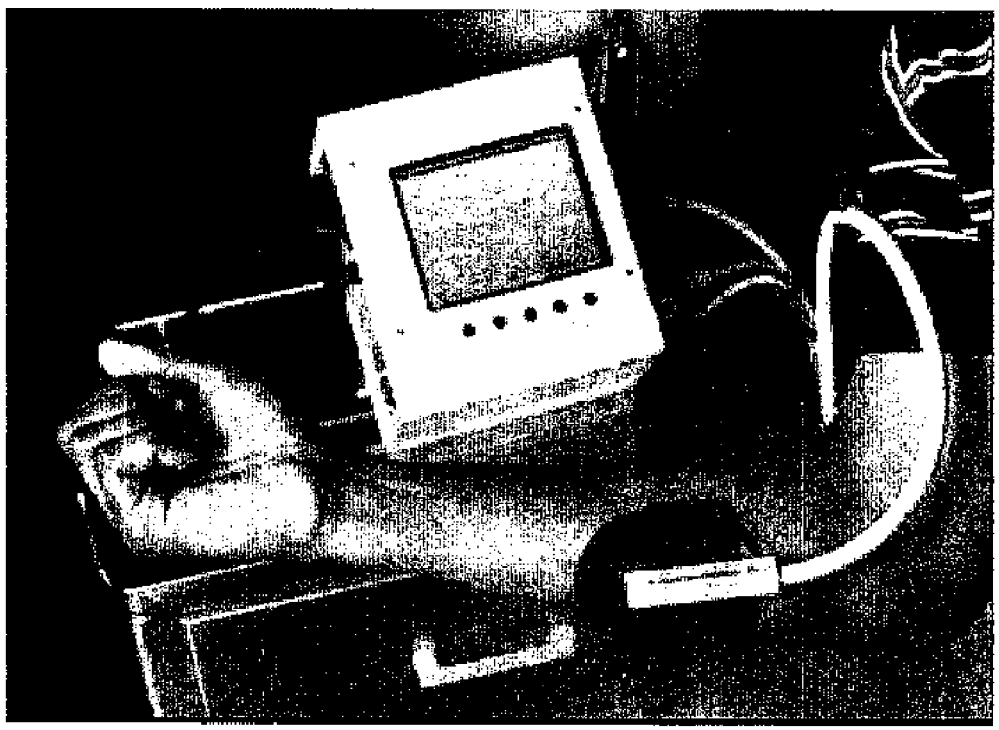
FIG. 13 is an image of an embodiment of a near-infrared reflectance spectrometer system.

To evaluate the effects of PCA loading corrections on measured spectral reflectance data, a set of reflectance spectra were collected from human subjects performing a handgrip exercise, and multi-subject venous blood pH models were developed and evaluated based on the reflectance measurements. The handgrip exercise protocol included a 2 second contraction of a subject's hand, followed by a 1 second relaxation, at four different effort levels: 15% maximum voluntary contraction (MVC), 30% MVC, 45% MVC, and 60% MVC. As exercise intensity increases, pH falls to a lower level at the end of each exercise bout. Each bout was 5 minutes in length, and bouts were conducted 40 minutes apart. Blood was drawn from a venous catheter placed in a vein close to the measurement muscle. Samples were obtained just prior to each bout (to provide a baseline pH measurement), every minute during the exercise bout, and at 5, 10, and 20 minutes post-exercise. Blood samples were measured using an I-Stat CG4+ cartridge (available from i-STAT, East Windsor, N.J.) to determine venous pH. Spectral reflectance measurements were made using an embodiment of spectrometer system 100 similar to the embodiment shown in FIG. 13.

Spectral reflectance data was measured from six different subjects. Accuracy of PLS-based pH prediction models was estimated before and after PCA loading correction of the spectral reflectance data using a "leave-one-subject-out" cross validation procedure. In this procedure, pH determinations for each subject are made based on a calibration equation developed from data measured for the other 5 subjects. Accuracy is estimated by calculating a root mean square error of prediction (RMSEP) between pH values obtained from NIRS reflectance measurements and from venous blood analysis.

Figure 14:
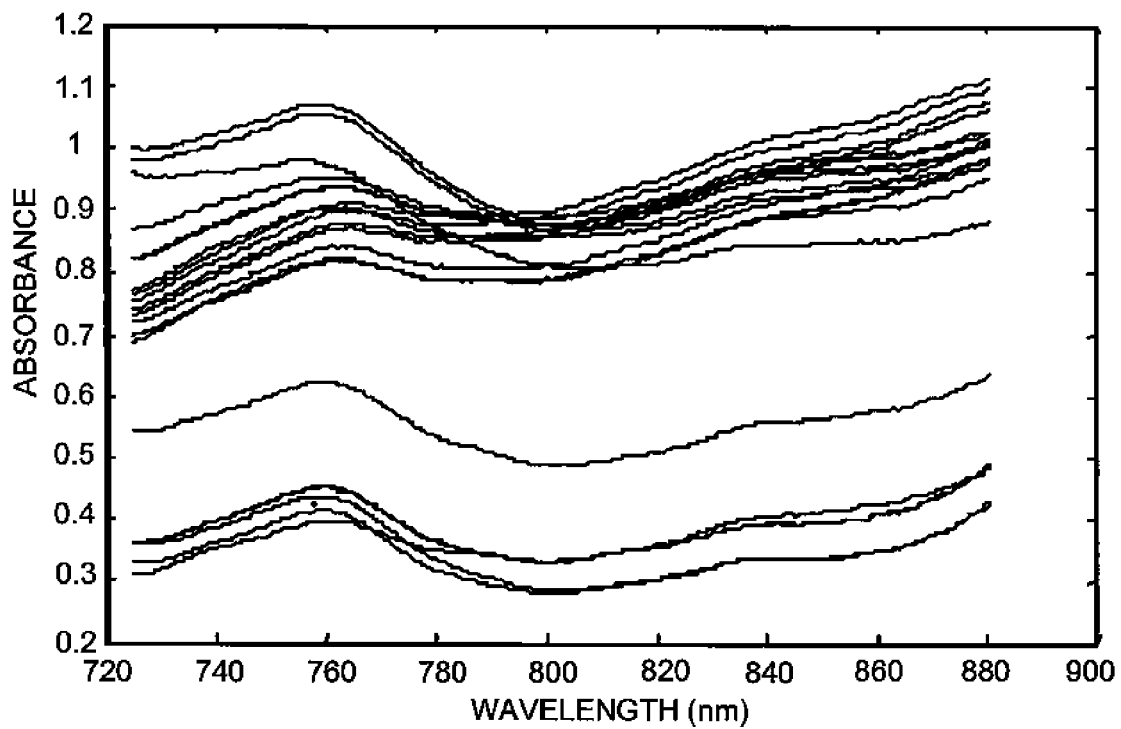
FIG. 14 is a graph showing a set of uncorrected spectral absorbance measurements from different human subjects.
Figure 15:
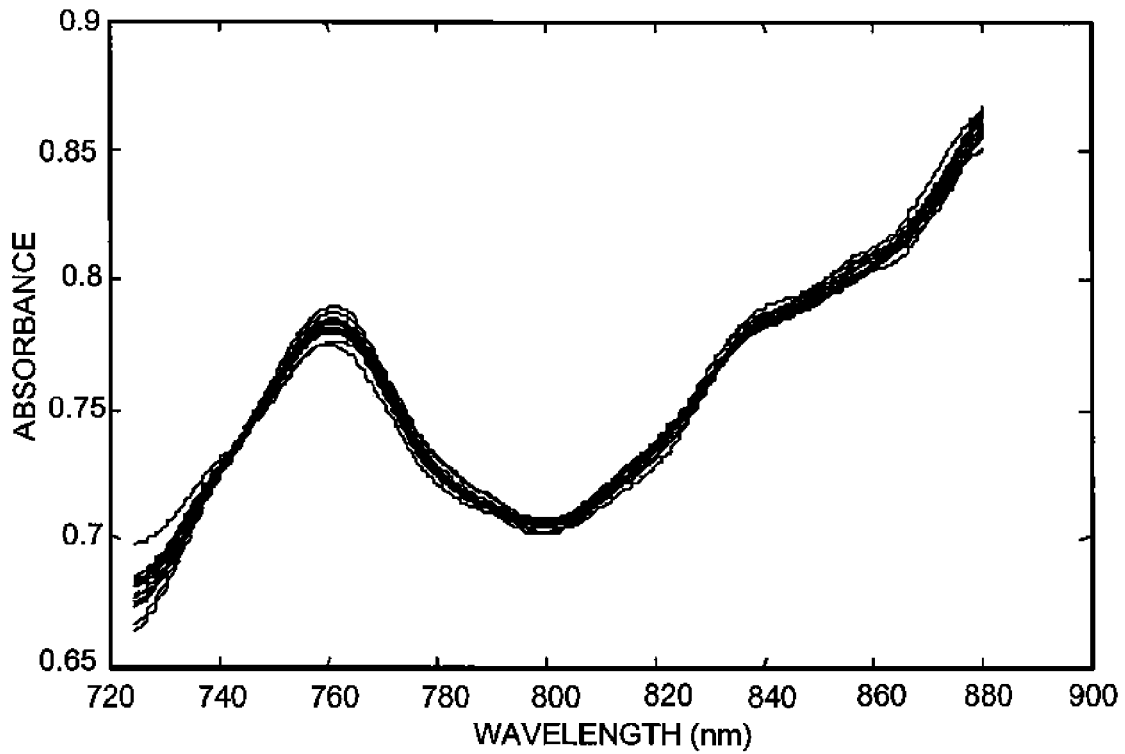
FIG. 15 is a graph showing a set of spectral absorbance measurements from different human subjects after application of a PCA loading correction algorithm.

FIG. 14 shows a set of calibration spectra from different subjects at a single pH value (about 7.35) before PCA loading corrections were applied. FIG. 15 shows the same set of calibration spectra after PCA loading corrections were applied. Following application of the correction procedure, the spectra at the same pH are nearly coincident. This is consistent with a reduction of subject-to-subject variations in the measured reflectance data which are not related to the analyte of interest, e.g., muscle pH.

Figure 16:
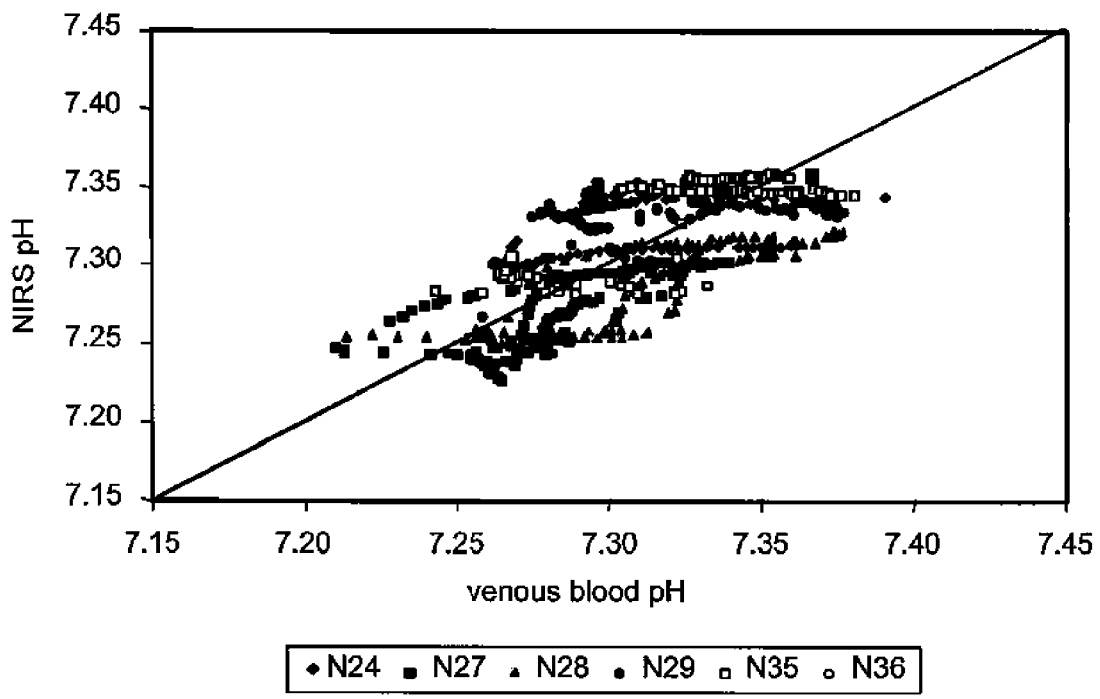
FIG. 16 is a graph showing predicted pH versus measured pH for a PLS model of pH based on uncorrected spectral absorbance data.

Calibration equations were developed using PLS from reflectance spectra and blood samples collected during the handgrip exercise bouts. Blood pH values were interpolated at time intervals corresponding to measured spectral data, where appropriate. FIG. 16 shows results of measured pH (for venous blood) versus predicted pH (from NIRS measurements) for uncorrected reflectance spectra, with calibration according to leave-one-subject-out cross-validation. The diagonal line in the figure indicates a perfect match between measured and predicted pH values. Predictions of pH based on uncorrected spectra have an average correlation, measured by coefficient of determination $R^2$, of about 0.44, indicating that a correspondence between measured and estimated pH values is not strong.

Figure 17:
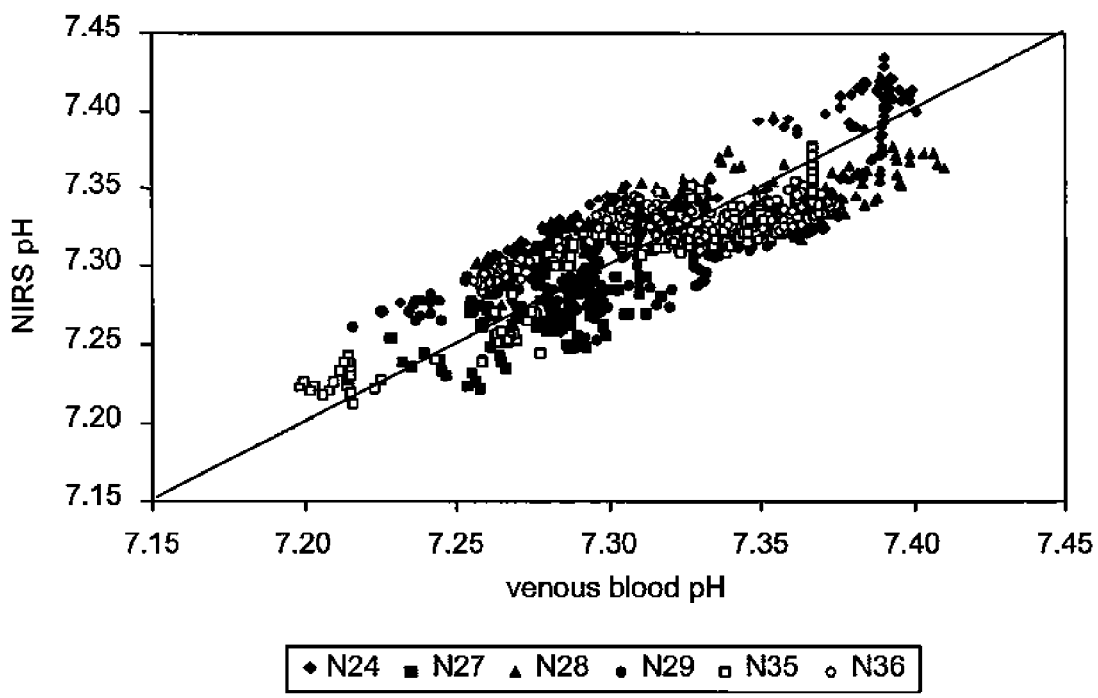
FIG. 17 is a graph showing predicted pH versus measured pH for a PLS model of pH based on spectra absorbance data corrected using a PCA loading correction method.

FIG. 17 shows results of measured pH versus predicted pH based on reflectance spectra that were corrected using PCA loading correction methods. The $R^2$ for the correspondence between measured and predicted pH values based on the corrected spectra is about 0.64 and the predicted pH values are more closely clustered along the diagonal line, indicating that the pH model based on the corrected spectra is significantly more accurate than the model of FIG. 16. The RMSEP is 0.025 pH units, which describes the observed scatter around the diagonal line.

Spectral Effects of Combined Correction Algorithms

Example 4

To evaluate the effects of combining multiple spectral correction algorithms, three-layer (e.g., skin, fat, and muscle) tissue-like solid phantoms were prepared. Agar (Agar A7049, available from Sigma-Aldrich Inc., St. Louis, Mo.) was used as a solid base material for the phantoms. Intralipid (available from Baxter Healthcare Corp., Deerfield, Ill.) was used as a scattering layer. Fabrication followed a procedure similar, for example, to the procedure described in R. Cubeddu et al., *Physics in Medicine and Biology* 42, 1971 (1997), the entire contents of which are incorporated herein by reference, except that different absorbers were used. Each layer was fabricated separately, and then skin and fat layers were placed on top of the muscle layer.

Each phantom included a 1.0 mm thick skin layer with 0.15 mg/mL melanin (Melanin M8631, available from Sigma-Aldrich Inc., St. Louis, Mo.) as an absorber. Absorbers in the muscle layer were a 2.2% solution of $6 \times 10^{-4}$ mL/mL India ink (available from Scientific Device Lab Inc., Des Plaines, Ill.) and NIR dye ADS780WS (available from American Dye Source, Inc., Quebec, Canada) of varied concentrations.

The concentration of the India ink was selected based on the concentration of blood in tissue, which is approximately 2.2%. The NIR dye has an absorption maximum at a wavelength of about 780 nm, similar to deoxygenated hemoglobin, while India ink has relatively wavelength-independent absorption properties. No absorber was introduced into the fat layer since human fat typically has a very low absorption coefficient. Reduced scattering coefficients ($\mu_s'$) for skin and fat were 1.5 mm$^{-1}$ and 1.2 mm$^{-1}$, respectively. Tissue phantoms were prepared so that each phantom had a muscle-reduced scattering coefficient ($\mu_s'$) of 0.5 mm$^{-1}$, 0.65 mm$^{-1}$, or 0.8 mm$^{-1}$, a fat thickness of 2.0 mm, 4.0 mm, or 6.0 mm, and a muscle dye concentration of: 6.67 µg/mL, 9.08 µg/mL, 13.31-µg/mL, 15.76 µg/mL, 17.92 µg/mL, 20.22 µg/mL, 22.58 µg/mL, 24.82 µg/mL, or 26.68 µg/mL. Sets of tissue phantoms having one of the foregoing muscle dye concentration were fabricated so that each member of the set had one of the 3 different levels of fat thickness and one of the 3 different muscle scattering coefficients, e.g., nine different phantoms were prepared with the same muscle dye concentration. The phantoms were fabricated in three groups of 27 phantoms with low, medium or high muscle dye concentrations, over a period of 3 days. Samples were sealed with plastic to avoid water loss, covered with aluminum foil to avoid photobleaching, and stored in a refrigerator to be measured in random order the day after fabrication.

Reflectance spectra of each of the phantoms at 2.5 mm and 30 mm source-detector (SD) separations were measured using system 100. An 8.5 W tungsten lamp (model 7106-003, available from Welch-Allyn Corp., Skaneateles, N.Y.) was used for illumination of the phantoms, and a spectrometer (USB2000, available from Ocean Optics Inc., Dunedin, Fla.) was used to collect spectral reflectance data. The two-distance probe of system 100 had one detector fiber bundle and two source fiber bundles 30 mm (long distance) and 2.5 mm (short distance) away from the detector bundle. A diameter of the detector fiber bundle was 1.0 mm, and diameters of the source fiber bundles at the long distance and at the short distance were 3.5 mm and 1.0 mm, respectively. During collection of reflectance spectra, the detector bundle was connected to the spectrometer, while the two source fiber bundles were connected to the lamp via an on-axis, or off-axis orientation. Computer controlled shutter system 110 was placed in front of the lamp to switch between the two source fiber positions so that only a single source fiber bundle was illuminated by the lamp.

Reflectance spectra collected at the short distance (2.5 mm SD) captured information from substantially only the skin and fat layers of the phantoms. Spectra collected at the long distance (30 mm SD) included spectral information from the skin, fat, and muscle layers.

Phantoms were separated into calibration and test sample sets. Samples in the calibration set were chosen with properties that were different from those in the calibration set to test PLS model predictions on samples which may have been poorly and/or incompletely modeled during calibration. Specifically, phantoms with a fat thickness of 2.0 mm and various dye concentrations and muscle scattering coefficients (a total of 27 phantoms) were used as the test samples. The remaining samples (a total of 54 phantoms) with fat thicknesses of 4.0 mm or 6.0 mm for each of the various dye concentrations and muscle scattering coefficients were used for calibration. None of the calibration samples had a fat layer with a thickness of 2.0 mm, and none of the test samples had a fat layer with a thickness of 4.0 mm or 6.0 mm.

A PLS model for dye concentration in the phantom muscle was created using calibration sample data, and the model was validated by predicting muscle dye concentrations from test sample spectra. Leave-one-out cross-validation was used to determine the number of PLS model factors. To evaluate the various spectral correction methods, PLS regressions were performed with and without PCA loading corrections and/or short-distance corrections and/or SNV scaling corrections. Data within a spectral wavelength range from 700 nm to 900 nm was used in the analysis. Prediction accuracy of the PLS models was described by $R^2$ (the coefficient of determination) between the estimated and actual dye concentrations, and an estimated measurement error, which was calculated as a root mean squared error of prediction (RMSEP) according to:

$$\text{RMSEP} = [(1/N)\Sigma_{i=1}^{N}(\hat{y}_i - y_i)^2]^{1/2} \quad (6)$$

where N is a number of test samples, and $\hat{y}_i$ and $y_i$ are the estimated and actual dye concentrations. A large $R^2$ value and a low RMSEP indicate that the PLS model accurately predicts dye concentration in the phantom samples.

Various spectral correction and data analysis algorithms were implemented in programs written in version 7.0 of the Matlab™ programming language (available from The Mathworks Inc., Natick, Mass.) and the version 3.5 of PLS_Toolbox™ (available from Eigenvector Research Inc., Manson, Wash.).

In the following examples, where short-distance corrections are applied to reflectivity spectra in combination with other spectral correction methods, the short-distance corrections are applied first. Where PCA loading corrections are applied to reflectivity spectra in combination with other spectral correction methods, the PCA loading corrections are applied last. For example, where short-distance, SNV, and PCA loading corrections are applied to spectral data, the short-distance corrections are applied first, followed by the SNV corrections, and finally the PCA loading corrections are applied.

Six calibration samples with the same dye concentration (e.g., n=6) were used to obtain PCA loadings for PCA loading correction of spectral data. The dye concentration at which the PCA loadings were obtained will be referred to as the "calibration" dye concentration subsequently. Loadings were obtained from PCA on sets of six calibration samples, with each set of six samples having one of nine different selected dye concentrations. Reflectance spectra for each set of six samples were corrected using different combinations of spectral correction methods to examine the effect of the methods and their parameters on the calculated loading vectors. To determine the number of loading vectors used in PCA loading correction, leave-one-out cross-validation calibration procedures were used in PLS models for dye concentration in the phantom samples. Calibration was performed using 1, 2, 3, 4, and 5 PCA loading vectors at each of the selected dye concentrations. The number of loading vectors and the selected dye concentration which produced the smallest root mean squared error of cross-validation (RMSECV) were selected for evaluation of the spectral correction methods. Analysis of the phantoms determined that the first four loading vectors obtained from PCA on the calibration spectra with a dye concentration of 20.22 µg/mL, provided the best prediction results for the test samples. The three spectral correction methods—short-distance overlayer correction, SNV correction, and PCA loading correction—were compared individually and in combination under the above conditions.

Figure 18:
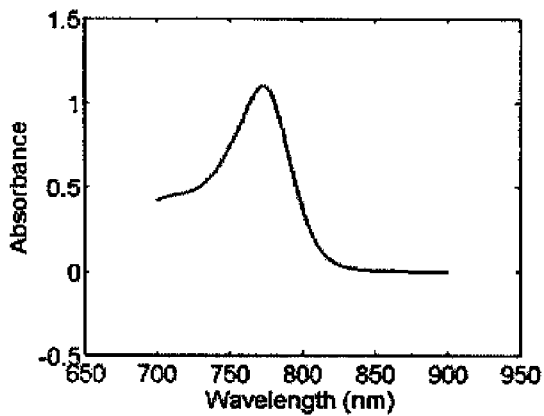
FIG. 18 is a graph showing an aqueous absorption spectrum for the dye ADS780WS.
Figure 19:
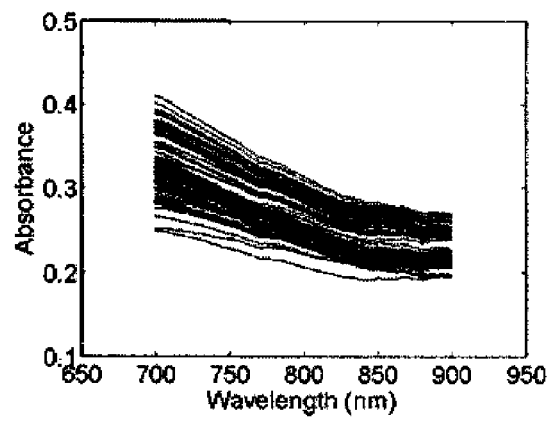
FIG. 19 is a graph showing short distance absorption spectra for a set of tissue-like phantom samples.
Figure 20:
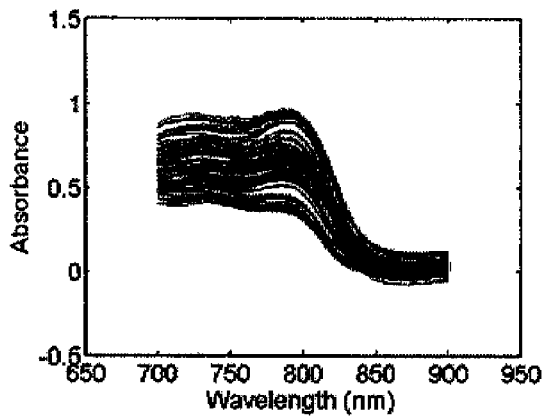
FIG. 20 is a graph showing long distance absorption spectra for a set of tissue-like phantom samples.
Figure 21:
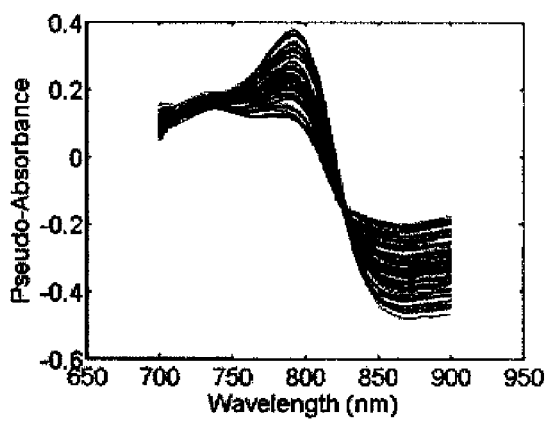
FIG. 21 is a graph showing long distance absorption spectra for a set of tissue-like phantom samples after short-distance corrections have been applied.

FIG. 18 shows an absorption spectrum of the ADS780WS dye in aqueous solution. FIGS. 19 and 20 show phantom absorbance spectra for short distance (e.g., 2.5 mm) and long distance (e.g., 30 mm) illumination of the phantoms, respectively. FIG. 21 shows long distance absorbance spectra corrected by applying short-distance correction methods, as discussed previously. The short distance absorbance spectra in FIG. 19 include reflected light from only the skin and fat layers overlying the muscle layer in the phantoms. The downward-sloping shapes of the absorbance curves are characteristic of the absorber melanin in the skin layer. Further, baseline shifts among the various curves are due to different fat layer thicknesses among the various phantoms.

Long distance spectra in FIG. 20 have spectral shapes that are similar to the dye solution spectrum shown in FIG. 18. The long distance spectra include contributions from light reflected from phantom muscle layers, where the dye is located. Variations in absorbance, e.g., between 700 nm and 750 nm, are due to a superposition of skin absorption and fat and muscle scattering effects on the dye absorption. Short-distance corrections reduce and/or remove skin absorption and fat scattering effects from the spectral absorbance data. As shown in FIG. 21, the resulting corrected spectra are more nearly coincident and resemble more closely the spectrum shown in FIG. 18 than the uncorrected spectra in FIG. 20. However, baseline variations that are attributed to variations in optical properties of the muscle layer (e.g., variability in muscle layer scattering) between samples. PCA loading correction algorithms can be used to reduce or remove variations that arise from the non-uniformity of the optical properties of the muscle layer among the phantoms.

Figure 22:
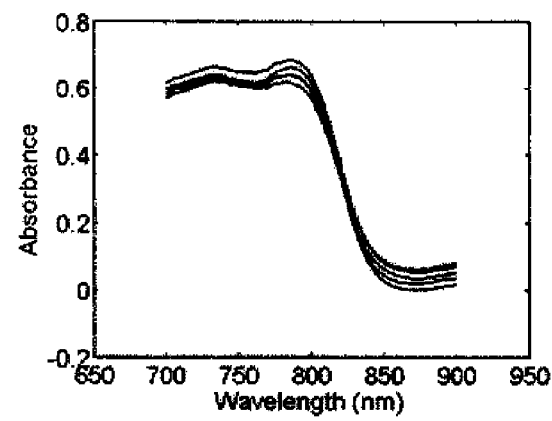
FIG. 22 is a graph showing uncorrected spectral absorbance measurements from a set of tissue-like phantom samples.

FIGS. 22-27 show absorbance spectra of six calibration samples, each with dye concentration 20.22 µg/mL, but with different combinations of fat layer thickness (4.0 mm or 6.0 mm) and muscle scattering coefficient (0.5 mm$^{-1}$, 0.65 mm$^{-1}$, or 0.8 mm$^{-1}$). FIG. 22 shows uncorrected absorbance spectra. If spectral effects due to fat and muscle scattering and skin absorption were perfectly corrected among the various phantoms, spectra corresponding to the same dye concentration would be overlapped. In the spectra shown in FIG. 22, some baseline shift and flattening is observed between 700 nm and 800 nm, and is attributable to these scattering and absorption effects.

Figure 23:
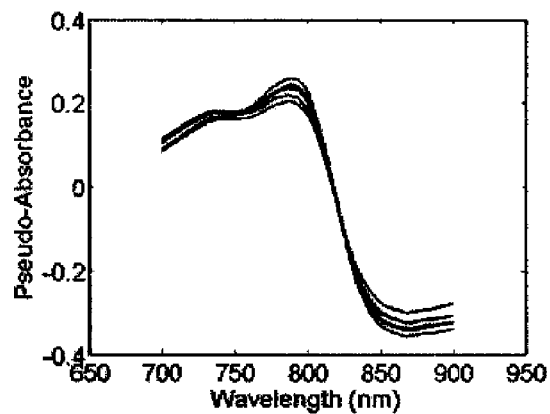
FIG. 23 is a graph showing spectral absorbance measurements from a set of tissue-like phantom samples after short-distance corrections have been applied.

FIG. 23 shows spectra from FIG. 22 after short-distance corrections for the overlying skin and fat layers have been applied to the spectra. The corrected spectra are closer to one another as a result of the applied correction, and have shapes that more closely resemble the absorption band of FIG. 18. However, there are still some differences among the corrected spectra, e.g., in the spectral region near the absorption peak at about 780 nm. These variations arise from muscle layer scattering, which is not corrected by short-distance algorithms and methods.

Figure 24:
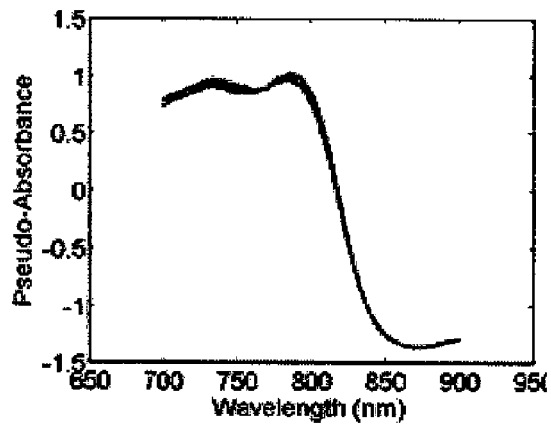
FIG. 24 is a graph showing spectral absorbance measurements from a set of tissue-like phantom samples after SNV scaling corrections have been applied.

FIG. 24 shows spectra from FIG. 22 after SNV scaling corrections have been applied. The spectra are closer together following application of the SNV methods, but a relatively flat shape of the spectra indicates that skin and fat absorption and scattering are not corrected by the SNV methods alone. In general, SNV methods can be used to reduce and/or remove scattering differences among multiple samples when variation among sample spectra arises primarily from scattering, rather than analyte variation.

Figure 25:
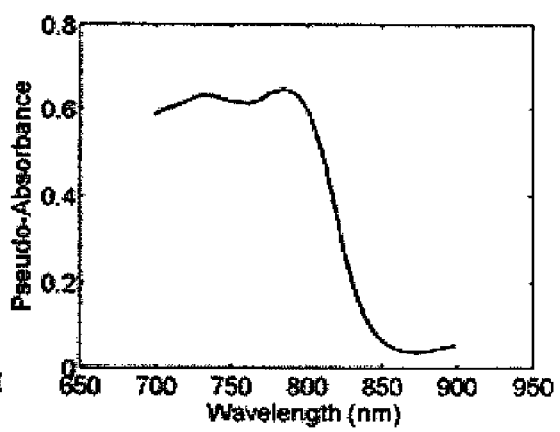
FIG. 25 is a graph showing spectral absorbance measurements from a set of tissue-like phantom samples after PCA loading corrections have been applied.

FIG. 25 shows spectra from FIG. 22 after PCA loading corrections have been applied to the spectra. Four loadings obtained from PCA of calibration samples with dye concentrations of 20.22 μg/mL were used to correct the absorbance spectra shown in FIG. 22. The corrected spectra, shown in FIG. 25, are closer together than the original uncorrected spectra. However, the corrected spectra still show spectral features that are attributable to melanin absorption in the skin layer of the samples.

Figure 26:
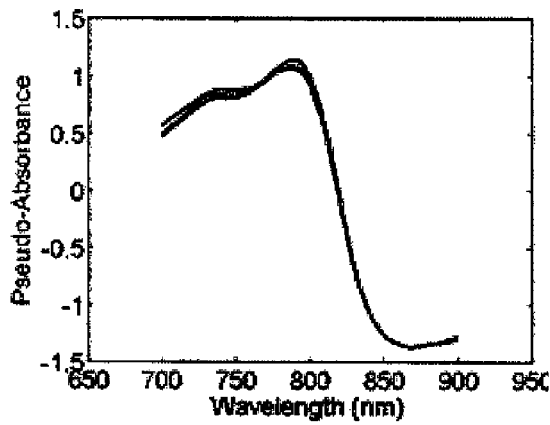
FIG. 26 is a graph showing spectral absorbance measurements from a set of tissue-like phantom samples after short-distance corrections and SNV scaling corrections have been applied.

Combinations of the various correction methods can also be applied to the absorbance spectra. FIG. 26 shows spectra from FIG. 22 after short-distance corrections and then SNV scaling corrections were applied in succession. Compared with the short-distance-corrected spectra of FIG. 23, the spectra in FIG. 26 are closer together and baseline variations are reduced, but are still present.

Figure 27:
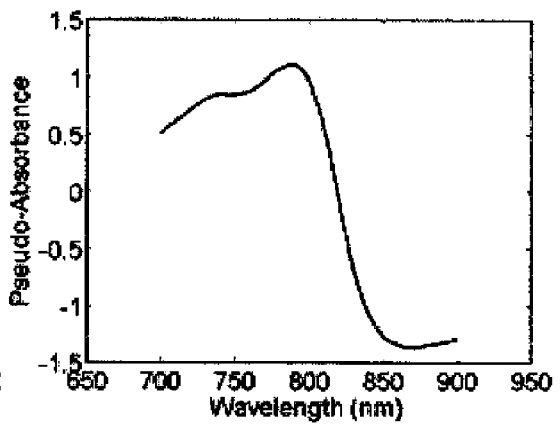
FIG. 27 is a graph showing spectral absorbance measurements from a set of tissue-like phantom samples after short-distance corrections, SNV scaling corrections, and PCA loading corrections have been applied.

FIG. 27 shows spectra from FIG. 22 after short-distance corrections, SNV scaling corrections, and PCA loading corrections were applied in succession. The spectra in FIG. 27 are highly overlapped, and their shapes resemble relatively closely the dye spectrum shown in FIG. 18 in the short wavelength region from 700 nm to 780 nm. Application of all three correction methods to the spectral absorbance data significantly reduced spectral contributions from skin and fat layer absorption and scattering, and different muscle scattering coefficients arising from analyte-irrelevant variations in optical properties of the muscle layer.

PLS predictive models were constructed based on calibration data and used to predict values of dye concentration in test samples. Spectral absorbance data for the calibration and test samples was either uncorrected, or corrected by applying short-distance corrections only, SNV scaling corrections only, PCA loading corrections only, a combination of short-distance and SNV scaling corrections, a combination of short-distance and PCA loading corrections, a combination of SNV scaling and PCA loading corrections, or a combination of short-distance, SNV scaling, and PCA loading corrections. A summary of model prediction results is shown in Table 4. Each PLS model has large values of $R^2$ (equal to or greater than 0.95), indicating that a strong correlation exists between predicted and measured dye concentrations. Without any spectral processing, even though predicted and measured dye concentrations were highly correlated, large prediction errors resulted: the RMSEP was 4.31 μg/mL, corresponding to an error of 21.54% of the total concentration range (from 26.68 μg/mL to 6.67 μg/mL).

With short-distance corrections only, SNV scaling corrections only, or PCA loading corrections only, the RMSEP of the PLS model decreased. Combinations of two different correction methods further decreased the RMSEP of the PLS model, and combining all three correction methods resulted in a PLS model with the lowest RMSEP, 1.08 μg/mL, a 5.3% percentage error, and a 3-fold decrease in RMSEP relative to a PLS model where no correction methods were used.

TABLE 4

| Spectral Correction Methods | $R^2$ | RMSEP (μg/mL) | Percentage Error | Number of Factors |
|---|---|---|---|---|
| None | 0.96 | 4.31 | 21.5 | 7 |
| Short-Distance Only | 0.97 | 3.86 | 19.3 | 7 |
| SNV Scaling Only | 0.97 | 3.16 | 15.8 | 2 |
| PCA Loading Only | 0.95 | 3.66 | 18.3 | 6 |
| Short-Dist. + SNV | 0.96 | 2.55 | 12.7 | 2 |
| Short-Dist. + PCA | 0.96 | 2.69 | 13.4 | 3 |
| SNV + PCA | 0.97 | 1.88 | 9.4 | 6 |
| Short-Dist. + SNV + PCA | 0.97 | 1.08 | 5.3 | 4 |

In certain embodiments, using spectral correction methods can reduce a number of factors used in a PLS model. For example, when PCA loading corrections were used along or in combination with the other correction methods, the number of model factors was less than the 7 factors used in a model based on uncorrected spectral absorbance data. As an example, when the three correction methods were used in combination, the PLS model for dye concentration in the muscle layer of samples used 4 model factors. This reduction in the number of factors for the concentration model was achieved because correction of the spectral data removed variations due to skin color, fat layer thickness, and muscle layer optical properties that would otherwise have been modeled with PLS regression.

Figure 28:
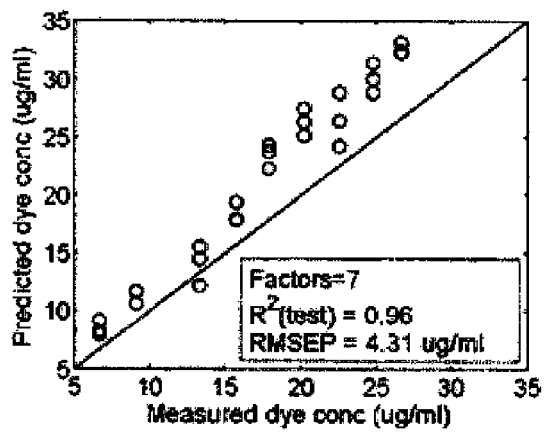
FIG. 28 is a graph showing prediction results for a PLS model of dye concentration based on uncorrected spectral absorbance data.
Figure 29:
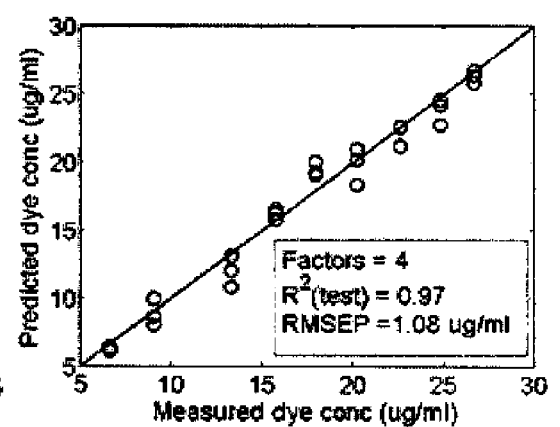
FIG. 29 is a graph showing prediction results for a PLS model of dye concentration based on spectral absorbance data corrected using three different correction methods.

Model prediction results are shown in FIG. 28 with no correction of the spectra absorbance data, and in FIG. 29 with correction of the spectral data using a combination of short-distance, SNV scaling, and PCA loading corrections. The diagonal line in each figures represents perfect prediction. Comparing FIGS. 28 and 29, after correcting the spectra data using three different correction methods, prediction results are more closely clustered along the diagonal unity line, and the predictive value of the PLS model is greater.

Example 5

The spectral correction methods disclosed herein have also been applied to human tissue spectra. For example, where spectra corresponding to different subjects, each having the same value of a particular analyte of interest are available, PCA loading corrections can be used to improve PLS models based on the spectra. As an example, a range of pH values can be obtained for a subject during periods of exercise. In general, muscle and blood pH decreases during exercise as lactic acid is produced, and then pH returns rapidly to baseline values when exercise is halted. If absorbance spectra are recorded continuously during periods of exercise and muscle and/or blood pH is simultaneously monitored, it is possible to obtain spectral data at different times that corresponds to the same pH value from different subjects performing a similar exercise protocol.

To evaluate the PCA loading correction method on spectral data from human subjects, a set of spectra and blood pH measurements were collected from the forearms of three human subjects performing a repetitive handgrip exercise protocol. Each subject squeezed a test device for 4 seconds, then relaxed for 2 seconds, repeating this pattern for a total duration of 5 minutes. Each subject performed four different exercise protocols at different, successively increasing force levels, with a 30 minute rest period between each protocol.

Figure 30:
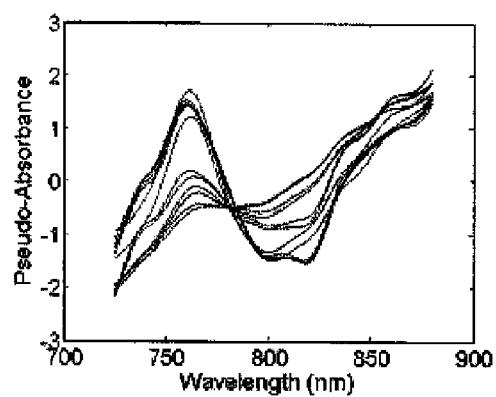
FIG. 30 is a graph showing spectral absorbance data recorded from different subjects at similar pH levels, and corrected using short-distance and SNV scaling correction methods.
Figure 31:
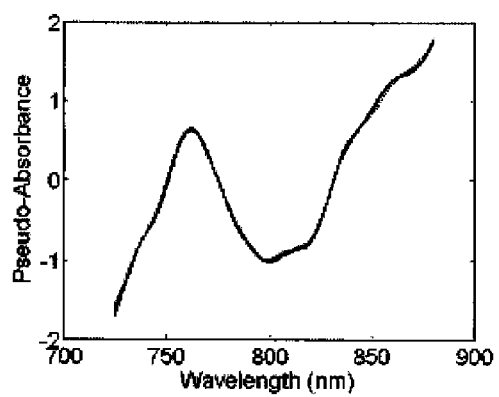
FIG. 31 is a graph showing the spectral absorbance data of FIG. 30, further corrected using PCA loading correction methods.

FIG. 30 shows a set of absorbance spectra collected from the three human subjects at time points during the exercise protocols where the blood pH of each subject was 7.37±0.001. Short-distance and SNV scaling corrections have been applied to the set of spectral data. FIG. 31 shows the same set of absorbance spectra shown in FIG. 30 after PCA loading corrections have been further applied. The absorbance spectra in FIG. 31 have been orthogonalized with the first four loading vectors obtained from PCA of the spectra in FIG. 30. After PCA loading correction of the spectral data, spectra from different subjects were significantly more overlapped, indicating that spectral contributions due to optical property variations in muscle tissues from one subject to another, which were not correlated with pH, were significantly reduced.

Figure 32:
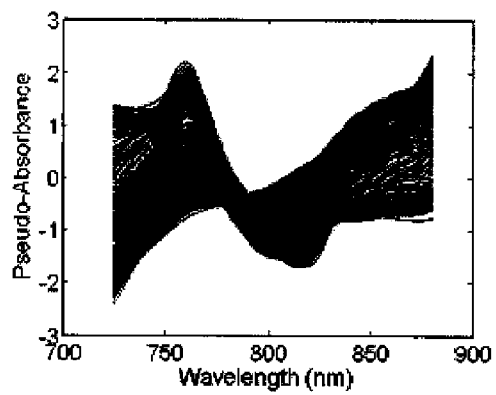
FIG. 32 is a graph showing spectral absorbance data recorded from different subjects at different pH values and corrected using short-distance and SNV scaling correction methods.
Figure 33:
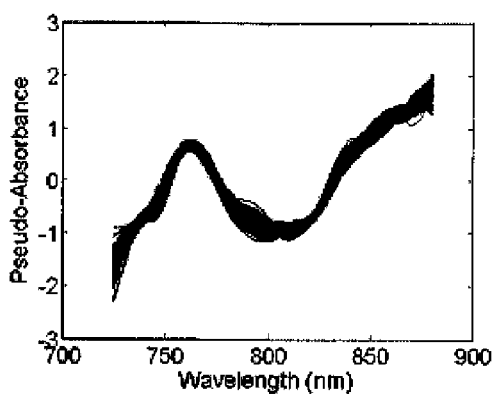
FIG. 33 is a graph showing the spectral absorbance data of FIG. 32, further corrected using PCA loading correction methods.

FIG. 32 shows all of the spectra from each of the three human subjects during periods of exercise at all measured pH values. Short-distance and SNV scaling corrections have been applied to the spectral data. FIG. 33 shows the data from FIG. 32 after PCA loading corrections have been further applied. The data was orthogonalized with the first four loading vectors obtained from PCA of the calibration spectra in FIG. 30 that correspond to a pH of 7.37±0.001. Application of PCA loading corrections significantly reduced variations in the spectra due to subject-to-subject variations in muscle tissue optical properties. Variations among the spectra shown in FIG. 33 correspond nominally to absorbance variations resulting from exercise-induced changes in muscle pH levels.

Other Embodiment

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A measurement system, comprising:
   (a) a light source;
   (b) a detection system;
   (c) a set of at least first, second, and third light ports, which set transmits light from the light source to a sample and receives and directs light reflected from the sample to the detection system, wherein a distance between the first port and the third port comprises a first detection distance and a distance between the second port and the third port comprises a second detection distance, wherein the first detection distance is larger than the second detection distance; and wherein either (i) the first and second ports are transmitting ports and the third port is a receiving port, or (ii) the first and second ports are receiving ports and the third port is a transmitting port; and
   wherein the detection system generates a first set of data corresponding to the first detection distance and comprising information corresponding to both an internal target within the sample and features overlying the internal target, and a second set of data corresponding to the second detection distance and comprising information corresponding to features overlying the internal target; and
   (d) a processor configured to remove information characteristic of the overlying features from the first set of data using the first and second sets of data to produce corrected information representing the internal target.

2. The system of claim 1, wherein the set of at least first, second, and third ports is situated on a single probe.

3. The system of claim 1, wherein the detection system is a spectral detection system, the first and second sets of data comprise first and second sets of spectra, and wherein the processor removes spectral information characteristic of the overlying features from the first set of spectra using the first and second sets of spectra to produce corrected spectral information representing the internal target.

4. The system of claim 1, wherein the second detection distance is between about 1 mm and about 5 mm.

5. The system of claim 1, wherein the second detection distance is between about 1.5 mm and about 3.5 mm.

6. The system of claim 1, wherein the first detection distance is greater than about 10 mm.

7. The system of claim 1, further comprising a shutter system for controlling whether light from the first or second transmitting port illuminates the sample.

8. The system of claim 3, wherein the spectral detection system comprises a spectrometer configured to receive light and to generate sets of spectra from the received light.

9. The system of claim 3, wherein the spectral detection system comprises a first spectrometer configured to receive light from the first receiving port and to generate the first set of spectra, and a second spectrometer configured to receive light from the second receiving port and to generate the second set of spectra.

10. The system of claim 2, wherein the probe head comprises a thermally conductive material to dissipate heat from the sample.

11. The system of claim 1, further comprising a thermally-conductive bridge between light transmitting ports and light receiving ports.

12. The system of claim 3, wherein the processor is further configured to remove spectral information from the first set of spectra that is characteristic of variations in optical scattering properties of the internal target that are unrelated to an analyte of interest therein.

13. The system of claim 3, wherein the processor is further configured to remove spectral information from the corrected spectral information representing the internal target that is characteristic of variations in optical scattering properties of the internal target that are unrelated to an analyte of interest therein.

14. The system of claim 1, wherein the light source provides light in the near-infrared region of the electromagnetic spectrum.

15. The system of claim 1, wherein the light source comprises at least one of an incandescent light source element, a light emitting diode, a laser diode, and a laser.

16. The system of claim 1, wherein the light source comprises an array of light emitting diodes.

17. The system of claim 3, wherein the processor is configured to remove spectral information characteristic of the overlying features from the first set of spectra using the first and second sets of spectra according to the equation $$\hat{R}_{ort} = R_{sfin} - \tilde{R}_{sj} w^T$$

where $R_{sfm}$ is a spectrum from the first set of spectra, $\tilde{R}_{sf}$ is a spectrum from the second set of spectra, w is a weight, "T" denotes a matrix transpose operation, and $\hat{R}_{ort}$ comprises corrected spectral information representing the internal target.

18. The system of claim 3, wherein the processor is configured to normalize the first and second sets of spectra with respect to one another prior to producing the corrected spectral information.

19. The system of claim 12, wherein the processor is configured to remove spectral information that is characteristic of variations in optical scattering properties of the internal target from the first set of spectra by orthogonalizing the first set of spectra with respect to a set of loading vectors of principal components determined from a set of spectra from a plurality of samples.

20. The system of claim 19, wherein the plurality of samples have a property of the internal target within a selected range.

21. The system of claim 19, wherein the processor is configured to orthogonalize the first set of spectra by performing a set of steps that comprise:
    performing a principal component analysis on a set of calibration spectra to determine a set of loading vectors corresponding to principal components of the calibration spectra;
    determining one or more orthogonalization factors from the principal component analysis;
    forming a loadings matrix having at least one dimension equal to the number of orthogonalization factors; and
    orthogonalizing the first set of spectra with respect to the loadings matrix.

22. A method for correcting information corresponding to an internal target within a sample measured by a system having a light source, a detection system, and a set of at least first, second, and third light ports, which set transmits light from the light source to the sample and receives and directs light reflected from the sample to the detection system, wherein a distance between the first port and the third port comprises a first detection distance and a distance between the second port and the third port comprises a second detection distance, wherein the first detection distance is larger than the second detection distance; and wherein either (i) the first and second ports are transmitting ports and the third port is a receiving port, or (ii) the first and second ports are receiving ports and the third port is a transmitting port, the method comprising:
    illuminating the sample with one or more light ports of the set;
    detecting the reflected light with the detection system;
    generating a first set of data corresponding to the first detection distance and comprising information corresponding to both an internal target within the sample and features overlying the internal target, and a second set of data corresponding to the second detection distance and comprising information corresponding to features overlying the internal target; and
    removing information characteristic of the overlying features from the first set of data using the first and second sets of data to produce corrected information representing the internal target.

23. The method of claim 22, wherein the detection system is a spectral detection system, the first and second sets of data comprise first and second sets of spectra, and wherein removing information characteristic of the overlying features from the first set of data comprises removing spectral information characteristic of the overlying features from the first set of spectra using the first and second sets of spectra to produce corrected spectral information representing the internal target.

24. The method of claim 23, wherein removing spectral information characteristic of overlying features of the sample from the first set of spectra comprises combining the first and second sets of spectra according to the equation $$\hat{R}_{ort} = R_{sfm} - \tilde{R}_{sf} w^T$$

where $R_{sfm}$ is a spectrum from the first set of spectra, $\tilde{R}_{sf}$ is a spectrum from the second set of spectra, w is a weight, "T" denotes a matrix transpose operation, and $\hat{R}_{ort}$ comprises corrected spectral information representing the internal target.

25. The method of claim 23, further comprising normalizing the first and second sets of spectra relative to one another prior to producing the corrected spectral information.

26. The method of claim 25, wherein normalizing comprises applying a polynomial fit between the first and second sets of spectra.

27. The method of claim 26, wherein coefficients used in the polynomial fit are derived from first and second sets of spectra recorded from one or more reflectance standards.

28. The method of claim 23, further comprising processing the first set of spectra to remove spectral information characteristic of variations in optical properties of the internal target that are unrelated to an analyte of interest therein.

29. The method of claim 23, further comprising processing the corrected spectral information representing the internal target to remove spectral information that is characteristic of variations in optical scattering properties of the internal target that are unrelated to an analyte of interest therein.

30. The method of claim 28, wherein removing spectral information characteristic of variations in optical properties of the internal target that are unrelated to an analyte of interest therein comprises orthogonalizing the first set of spectra with respect to a set of loading vectors of principal components determined from a set of calibration spectra.

31. The method of claim 30, wherein orthogonalizing the first set of spectra with respect to a set of loading vectors comprises:
    performing a principal component analysis on a set of calibration spectra to determine a set of loading vectors corresponding to principal components of the set of calibration spectra;
    determining one or more orthogonalization factors from the principal component analysis;
    forming a loadings matrix having at least one dimension equal to the number of orthogonalization factors; and
    orthogonalizing the first set of spectra with respect to the loadings matrix.

32. A method of measuring an analyte in a subject, the method comprising:
    generating a set of corrected spectra based on reflectance measurements from an animal according to the method of claim 22;
    developing one or more calibration equations based on a relationship between a measurement of the analyte in the animal and the set of corrected spectra from the animal;
    generating a set of corrected spectra based on reflectance measurements from the subject according to the method of claim 22; and
    determining a value of the analyte in the subject based on the one or more calibration equations and the set of corrected spectra from the subject.

33. The method of claim 32, wherein the subject is a human.

34. The method of claim 32, wherein the sets of corrected spectra generated based on reflectance measurements from the animal and the subject are further processed to remove spectral information characteristic of variations in optical properties of internal targets is comprising the analyte.

35. A method of measuring an analyte in a subject, the method comprising:
generating a set of corrected spectra based on reflectance measurements from a first body site of the subject according to the method of claim 22;
developing one or more calibration equations based on a relationship between a measurement of the analyte at the first body site and the set of corrected spectra from the first body site;
generating a set of corrected spectra based on reflectance measurements from a second body site of the subject according to the method of claim 22; and
determining a value of the analyte at the second body site based on the one or more calibration equations and the set of corrected spectra from the second body site.

36. The method of claim 35, wherein the subject is a human, the first body site is an arm, and the second body site is a leg.

37. The method of claim 35, wherein the sets of corrected spectra generated based on reflectance measurements from the first and second body sites are further processed to remove spectral information characteristic of variations in optical properties of internal targets comprising the analyte.

* * * * *

UNITED STATES PATENT AND TRADEMARK OFFICE
CERTIFICATE OF CORRECTION

PATENT NO.       : 7,616,303 B2                              Page 1 of 1
APPLICATION NO.  : 11/411538
DATED            : November 10, 2009
INVENTOR(S)      : Yang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 474 days.

Signed and Sealed this

Nineteenth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,616,303 B2 | Page 1 of 1 |
| APPLICATION NO. | : 11/411538 | |
| DATED | : November 10, 2009 | |
| INVENTOR(S) | : Ye Yang et al. | |

It is certified that error appears in the above-identified patent and that said Letters Patent is hereby corrected as shown below:

In the specification

Column 1, line 22, replace "may have" with -- has --.

Signed and Sealed this
Eleventh Day of November, 2014

Michelle K. Lee
*Deputy Director of the United States Patent and Trademark Office*